United States Patent
Saito et al.

(10) Patent No.: US 7,902,220 B2
(45) Date of Patent: Mar. 8, 2011

(54) 8-AZABICYCLO[3.2.1]OCTYL-2-HYDROXYBENZAMIDE COMPOUNDS AS MU OPIOID RECEPTOR ANTAGONISTS

(75) Inventors: Daisuke Roland Saito, Burlingame, CA (US); Daniel D. Long, San Francisco, CA (US); Priscilla Van Dyke, San Francisco, CA (US); Timothy J. Church, San Mateo, CA (US); Lan Jiang, Foster City, CA (US); Bryan Frieman, San Diego, CA (US)

(73) Assignee: Theravance, Inc., South San Francisco, CA (US)

( * ) Notice: Subject to any disclaimer, the term of this patent is extended or adjusted under 35 U.S.C. 154(b) by 276 days.

(21) Appl. No.: 12/229,664

(22) Filed: Aug. 26, 2008

(65) Prior Publication Data

US 2009/0062333 A1 Mar. 5, 2009

Related U.S. Application Data

(60) Provisional application No. 60/966,364, filed on Aug. 27, 2007, provisional application No. 61/051,065, filed on May 7, 2008.

(51) Int. Cl.
*A61K 31/46* (2006.01)
*C07D 451/02* (2006.01)
*A61P 1/00* (2006.01)

(52) U.S. Cl. .................................. 514/304; 546/124
(58) Field of Classification Search ................. 546/124; 514/304

See application file for complete search history.

(56) References Cited

U.S. PATENT DOCUMENTS

| | | | |
|---|---|---|---|
| 5,159,081 A | 10/1992 | Cantrell et al. | |
| 6,313,312 B1 | 11/2001 | Banks et al. | |
| 6,469,030 B2 | 10/2002 | Farrar et al. | |
| 6,479,516 B1 | 11/2002 | Gibson et al. | |
| 6,593,348 B2 | 7/2003 | Carroll et al. | |
| 6,610,711 B2 | 8/2003 | Armer et al. | |
| 6,992,090 B2 | 1/2006 | Le Bourdonnec et al. | |
| 7,049,335 B2 | 5/2006 | McHardy et al. | |
| 7,087,749 B2 | 8/2006 | Dolle et al. | |
| 2002/0025948 A1 | 2/2002 | Banks et al. | |
| 2004/0186135 A1 | 9/2004 | Dolle et al. | |
| 2004/0204453 A1 | 10/2004 | McHardy et al. | |
| 2004/0254190 A1 | 12/2004 | Liras | |
| 2007/0105863 A1 | 5/2007 | Dolle et al. | |
| 2007/0219278 A1 | 9/2007 | Long et al. | |
| 2008/0207676 A1 | 8/2008 | Dalziel et al. | |
| 2009/0023934 A1 | 1/2009 | Colson et al. | |
| 2009/0062332 A1 | 3/2009 | Saito et al. | |
| 2009/0062334 A1 | 3/2009 | Long et al. | |
| 2009/0062335 A1 | 3/2009 | Long et al. | |

FOREIGN PATENT DOCUMENTS

| | | | |
|---|---|---|---|
| WO | 2004089908 | * | 10/2004 |
| WO | WO 2004/089908 A2 | | 10/2004 |
| WO | WO 2004/089909 A1 | | 10/2004 |
| WO | WO 2007/103187 A2 | | 9/2007 |

OTHER PUBLICATIONS

Le Bourdonnec et al., "*trans*-3,4-Dimethyl-4-(3-carboxamidophenyl)piperidines: A Novel Class of µ-Selective Opioid Antagonists", Bioorganic & Medicinal Chemistry Letters, vol. 13 pp. 4459-4462 (2003).
Le Bourdonnec et al., "Elucidation of the Bioactive Conformation of the *N*-Substituted *trans*-3,4-Dimethyl-4-(3-hydroxyphenyl)piperidine Class of µ-Opioid Receptor Antagonists", Journal of Medicinal Chemistry, vol. 49, pp. 7278-7289 (2006).
Le Bourdonnec et al., "Synthesis and Pharmacological Evaluation of Novel Octahydro-1*H*-pyrido[1,2-a]pyrazine as µ-Opioid Receptor Antagonists", Journal of Medicinal Chemistry, vol. 49, pp. 7290-7306 (2006).
Diaz et al., "SAR and Biological Evaluation of Novel *trans*-3,4-dimethyl-4-arylpiperidine Derivatives as Opioid Antagonists", Bioorganic & Medicinal Chemistry Letters, vol. 15 pp. 3844-3848 (2005).
Lu et al., "Substituted Bridged Phenyl Piperidines: Orally Active Growth Hormone Secretagogues", Bioorganic & Medicinal Chemistry Letters, 13, pp. 1817-1820 (2003).
International Search Report for PCT/US2008/010100.

* cited by examiner

*Primary Examiner* — D. Margaret Seaman
*Assistant Examiner* — Niloofar Rahmani
(74) *Attorney, Agent, or Firm* — Jeffrey A. Hagenah; Roberta P. Saxon

(57) ABSTRACT

The invention provides 8-azabicyclo[3.2.1]octyl-2-hydroxybenzamide compounds of formula (I):

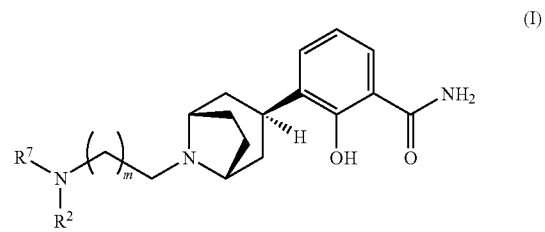

wherein $R^2$, $R^7$, and m are defined in the specification, or a pharmaceutically-acceptable salt thereof, that are antagonists at the mu opioid receptor. The invention also provides pharmaceutical compositions comprising such compounds, methods of using such compounds to treat conditions associated with mu opioid receptor activity, and processes and intermediates useful for preparing such compounds.

14 Claims, No Drawings

8-AZABICYCLO[3.2.1]OCTYL-2-HYDROXYBENZAMIDE COMPOUNDS AS MU OPIOID RECEPTOR ANTAGONISTS

CROSS-REFERENCE TO RELATED APPLICATIONS

This application claims the benefit of U.S. Provisional Application Nos. 60/966,364, filed on Aug. 27, 2007, and 61/051,065, filed on May 7, 2008, the disclosures of which are incorporated herein by reference in their entirety.

BACKGROUND OF THE INVENTION

1. Field of the Invention

The invention is directed to 8-azabicyclo[3.2.1]octane compounds which are useful as mu opioid receptor antagonists. The invention is also directed to pharmaceutical compositions comprising such compounds, methods of using such compounds for treating or ameliorating medical conditions mediated by mu opioid receptor activity, and processes and intermediates useful for preparing such compounds.

2. State of the Art

It is now generally understood that endogenous opioids play a complex role in gastrointestinal physiology. Opioid receptors are expressed throughout the body, both in the central nervous system and in peripheral regions including the gastrointestinal (GI) tract.

Compounds which function as agonists at opioid receptors, of which morphine is a prototypical example, are the mainstays of analgesic therapy for the treatment of moderate to severe pain. Unfortunately, use of opioid analgesics is often associated with adverse effects on the GI tract, collectively termed opioid-induced bowel dysfunction (OBD). OBD includes symptoms such as constipation, decreased gastric emptying, abdominal pain and discomfort, bloating, nausea, and gastroesophageal reflux. Both central and peripheral opioid receptors are likely involved in the slowdown of gastrointestinal transit after opioid use. However, evidence suggests that peripheral opioid receptors in the GI tract are primarily responsible for the adverse effects of opioids on GI function.

Since the side effects of opioids are predominantly mediated by peripheral receptors, whereas the analgesia is central in origin, a peripherally selective antagonist can potentially block undesirable GI-related side effects without interfering with the beneficial central effects of analgesia or precipitating central nervous system withdrawal symptoms.

Of the three major opioid receptor subtypes, denoted mu, delta, and kappa, most clinically-used opioid analgesics are thought to act via mu opioid receptor activation to exert analgesia and to alter GI motility. Accordingly, peripherally selective mu opioid antagonists are expected to be useful for treating opioid-induced bowel dysfunction. Preferred agents will demonstrate significant binding to mu opioid receptors in vitro and be active in vivo in GI animal models.

Postoperative ileus (POI) is a disorder of reduced motility of the GI tract that occurs after abdominal or other surgery. The symptoms of POI are similar to those of OBD. Furthermore, since surgical patients are often treated during and after surgery with opioid analgesics, the duration of POI may be compounded by the reduced GI motility associated with opioid use. Mu opioid antagonists useful for treating OBD are therefore also expected to be beneficial in the treatment of POI.

SUMMARY OF THE INVENTION

The invention provides novel compounds that possess mu opioid receptor antagonist activity.

Accordingly, the invention provides a compound of formula (I):

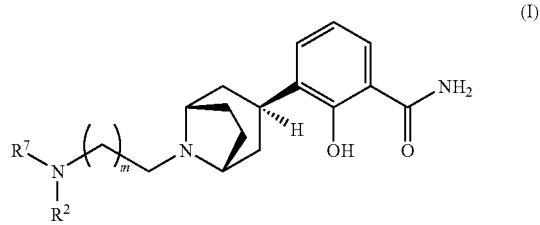

wherein:
$R^7$ is hydrogen or —$CH_2$—$R^1$;
$R^1$ is $C_{4-10}$ alkyl, $C_{3-12}$cycloalkyl, or phenyl, wherein $C_{3-12}$cycloalkyl and phenyl are each optionally substituted with one or two halo;
$R^2$ is selected from —C(O)$R^3$, —C(O)NH$R^4$, —C(O)O$R^5$, —S(O)$_2R^6$, and —C(O)$R^8$;
$R^3$ is $C_{1-6}$ alkyl substituted with one or two substituents selected from —O$R^a$, —S(O)$_2R^b$, and —C(O)$R^c$;
$R^4$ and $R^5$ are each independently $C_{1-6}$ alkyl substituted with one or two substituents selected from —O$R^a$ and —S(O)$_2R^b$;
$R^6$ is $C_{1-3}$alkyl;
$R^8$ is phenyl, optionally substituted with one or two halo;
$R^a$ is hydrogen or $C_{1-3}$alkyl;
$R^b$ is $C_{1-3}$alkyl;
$R^c$ is selected from hydrogen, $C_{1-3}$alkyl, and benzyl; and
m is 1 or 2;
provided that when $R^7$ is hydrogen, $R^2$ is —C(O)$R^8$;
or a pharmaceutically-acceptable salt thereof.

The invention also provides a pharmaceutical composition comprising a compound of the invention and a pharmaceutically-acceptable carrier.

The invention also provides a method of treating a disease or condition associated with mu opioid receptor activity, e.g. a disorder of reduced motility of the gastrointestinal tract such as opioid-induced bowel dysfunction and post-operative ileus, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate thereof, as a research tool for studying a biological system or sample or for discovering new compounds having mu opioid receptor activity, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with mu opioid receptor activity, e.g. a disorder of reduced motility of the gastrointestinal tract, in a mammal.

DETAILED DESCRIPTION OF THE INVENTION

The invention provides 8-azabicyclo[3.2.1]octane mu opioid receptor antagonists of formula (I), or pharmaceutically-acceptable salts or solvates thereof. The following substituents and values are intended to provide representative examples of various aspects of this invention. These representative values are intended to further define such aspects and are not intended to exclude other values or limit the scope of the invention.

In a specific aspect, $R^7$ is hydrogen or —$CH_2$—$R^1$.

In another specific aspect, $R^7$ is hydrogen.

In a specific aspect, $R^7$ is —$CH_2$—$R^1$ wherein $R^1$ is $C_{4-10}$ alkyl, $C_{3-12}$cycloalkyl, or phenyl, wherein $C_{3-12}$cycloalkyl and phenyl are each optionally substituted with one or two halo.

In another specific aspect, $R^7$ is —$CH_2$—$R^1$ wherein $R^1$ is $C_{4-6}$alkyl, $C_{3-6}$cycloalkyl, or phenyl, wherein $C_{3-6}$cycloalkyl and phenyl are each optionally substituted with one or two fluoro.

In other specific aspects, $R^7$ is —$CH_2$—$R^1$ wherein $R^1$ is $C_{4-6}$alkyl or $C_{3-6}$cycloalkyl, wherein $C_{3-6}$cycloalkyl is optionally substituted with one or two fluoro. Representative $R^1$ groups within this aspect include, but are not limited to, 1-ethylpropyl, tert-butyl, cyclopentyl, cyclohexyl, phenyl, 4,4-difluorocyclohexyl, 4-fluorocyclohexyl, 2,4-difluorophenyl, and the like. In yet another aspect, $R^7$ is —$CH_2$—$R^1$ wherein $R^1$ is 1-ethylpropyl, tert-butyl, cyclohexyl, or 4,4-difluorocyclohexyl.

In a specific aspect, $R^2$ is selected from —$C(O)R^3$, —$C(O)NHR^4$, —$C(O)OR^5$, —$S(O)_2R^6$, and —$C(O)R^8$.

In another specific aspect, $R^2$ is selected from —$C(O)R^3$, —$C(O)NHR^4$, —$C(O)OR^5$, and —$S(O)_2R^6$.

In another specific aspect, $R^2$ is selected from —$C(O)R^3$, —$C(O)NHR^4$, and —$S(O)_2R^6$.

In a specific aspect, $R^2$ is —$C(O)R^3$, wherein $R^3$ is $C_{1-6}$ alkyl substituted with one or two substituents selected from —$OR^a$, —$S(O)_2R^b$, and —$C(O)R^c$.

In a specific aspect, $R^2$ is —$C(O)R^3$ wherein $R^3$ is $C_{1-6}$ alkyl substituted with one or two substituents selected from —$OR^a$ and —$S(O)_2R^b$. In yet another specific aspect, $R^2$ is —$C(O)R^3$, wherein $R^3$ is $C_{1-3}$alkyl substituted with one or two —OH or with one —$S(O)_2CH_3$. Representative $R^2$ groups within this aspect include, but are not limited to, —$C(O)CH_2OH$, —$C(O)CH(OH)CH_2OH$, and —$C(O)CH_2S(O)_2CH_3$. In yet another specific aspect, $R^2$ is —$C(O)R^3$, wherein $R^3$ is $C_{1-3}$alkyl substituted with —$C(O)R^c$.

In still another specific aspect, $R^2$ is —$C(O)R^8$ where $R^8$ is phenyl optionally substituted with one or two substituents selected from fluoro and chloro.

In a specific aspect, $R^a$ is hydrogen or $C_{1-3}$alkyl. In another specific aspect, $R^a$ is hydrogen or methyl. In yet another specific aspect, $R^a$ is hydrogen.

In a specific aspect, $R^b$ is $C_{1-3}$alkyl. In another specific aspect, $R^b$ is methyl.

In a specific aspect, $R^c$ is hydrogen, $C_{1-3}$alkyl, or benzyl. In another specific aspect, $R^c$ is hydrogen or benzyl In a specific aspect, m is 1 or 2. In another specific aspect m is 1.

In yet another aspect, the invention provides a compound of formula (Ia):

(Ia)

wherein:

$R^1$ is $C_{4-10}$ alkyl, $C_{3-12}$cycloalkyl, or phenyl, wherein $C_{3-12}$cycloalkyl and phenyl are each optionally substituted with one or two halo;

$R^2$ is selected from —$C(O)R^3$, —$C(O)NHR^4$, —$C(O)OR^5$, and —$S(O)_2R^6$;

$R^3$, $R^4$, and $R^5$ are each independently $C_{1-6}$ alkyl substituted with one or two substituents selected from —$OR^a$ and —$S(O)_2R^b$;

$R^6$ is $C_{1-3}$alkyl;

$R^a$ is hydrogen or $C_{1-3}$alkyl;

$R^b$ is $C_{1-3}$alkyl; and m is 1 or 2;

or a pharmaceutically-acceptable salt thereof.

In still another aspect, the invention provides a compound of formula (Ib) or (Ic):

(Ib)

(Ic)

wherein $R^1$, $R^3$, $R^7$, and m take any of the values defined above.

The invention further provides the compounds of Examples 1-26 herein.

The chemical naming convention used herein is illustrated for the compound of Example 1:

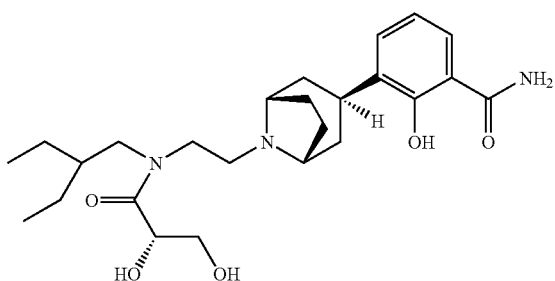

which is 3-endo-(8-{2-[((S)-2,3-dihydroxypropionyl)-(2-ethylbutyl)-amino]ethyl}-8-azabicyclo[3.2.1]oct-3-yl)-2-hydroxybenzamide. Alternatively, using the IUPAC conventions as implemented in AutoNom software, (MDL Information Systems, GmbH, Frankfurt, Germany), the compound is denoted 3-((1R,3R,5S)-8-{2-[((S)-2,3-dihydroxypropionyl)-(2-ethylbutyl)amino]ethyl}-8-azabicyclo[3.2.1]oct-3-yl)-2-hydroxy-benzamide. The names used herein therefore correspond to the IUPAC notation with the endo orientation of the substituted phenyl group with respect to the 8-azabicyclo[3.2.1]octane group indicated explicitly. All of the compounds of the invention are in the endo orientation. For convenience, as used herein, the term "8-azabicyclooctane" means 8-azabicyclo[3.2.1]octane.

In addition to the endo stereochemistry with respect to the bicyclo group, the compounds of the invention may contain a chiral center in the substituents $R^1$ and $R^3$. Accordingly, the invention includes racemic mixtures, pure stereoisomers, and stereoisomer-enriched mixtures of such isomers, unless otherwise indicated. When the stereochemistry of a compound is specified, including both the orientation with respect to the 8-azabicyclooctane group and the chirality in a substituent $R^1$ and/or $R^3$, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "cycloalkyl" means a monovalent saturated or partially saturated carbocyclic group which may be monocyclic or multicyclic. Unless otherwise defined, such cycloalkyl groups typically contain from 3 to 12 carbon atoms. Representative cycloalkyl groups include, by way of example, cyclopropyl (c-propyl), cyclobutyl (c-butyl), cyclopentyl (c-pentyl), cyclohexyl (c-hexyl), cycloheptyl (c-heptyl), cyclooctyl (c-octyl), adamantyl, cyclohexenyl, and the like.

The term "halo" means fluoro, chloro, bromo or iodo.

The term "compound" means a compound that was synthetically prepared or prepared in any other way, such as by in vivo metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of the invention of formula (Id), in which $R^2$ is defined as —C(O)$R^3$ or —C(O)$R^8$, are prepared as illustrated in Scheme A. (The substituents and variables shown in the following schemes have the definitions provided above unless otherwise indicated).

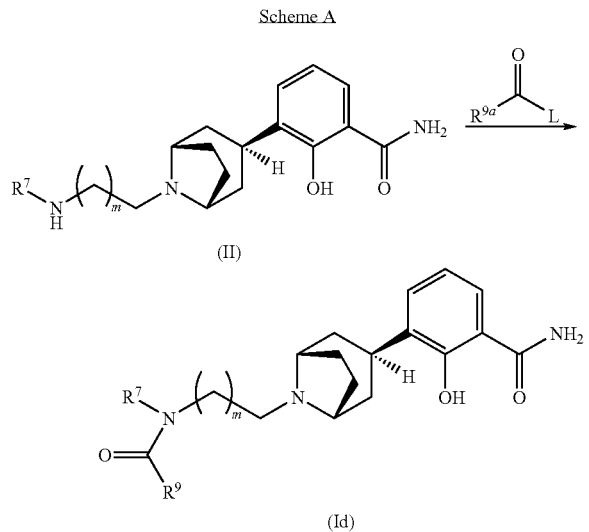

In Scheme A, $R^9$ represents $R^3$ or $R^8$, $R^{9a}$ represents $R^3$, a protected form of $R^3$, or $R^8$, and L represents a leaving group, such as chloro, or $R^{9a}$C(O)-L represents a carboxylic acid or a carboxylate salt. For example, to prepare a compound in which $R^3$ is —CH$_2$OH, a useful reagent is acetoxyacetyl chloride, in which $R^{9a}$ is —CH$_2$OC(O)CH$_3$ and L is chloro. When $R^{9a}$ is a protected form of $R^3$, the reaction also includes a deprotection step, which is not shown.

Optimal reaction conditions for the reaction of Scheme A may vary depending on the chemical properties of the reagent $R^{9a}$C(O)-L, as is well known to those skilled in the art. For example, when L is a halo leaving group, such as chloro, the reaction is typically conducted by contacting intermediate (II) with between about 1 and about 2 equivalents of a compound of formula $R^{9a}$C(O)-L in an inert diluent, such as dichloromethane. Optionally, the reaction is conducted in the presence of base, for example between about 2 and about 6 equivalents of base, such as N,N-diisopropylethylamine or triethylamine. Suitable inert diluents also include 1,1,2,2-tetrachloroethane, tetrahydrofuran, dimethylacetamide, and the like. The reaction is typically conducted at a temperature in the range of about −50° C. to about 30° C. for about a quarter hour to about 16 hours, or until the reaction is substantially complete.

When the reagent $R^{9a}$C(O)-L is a carboxylic acid or a carboxylate salt, the reaction is typically conducted by contacting intermediate (II) with between about 1 and about 5 equivalents of the acid $R^{9a}$C(O)OH or the carboxylate salt, for example, $R^{9a}$C(O)OLi, in an inert diluent, optionally in the presence of an excess of base, both as described above, and in the presence of between about 1 and about 6 equivalents of an activating agent such as N,N-carbonyl diimidazole (CDI), N,N,N',N'-tetramethyl-O-(7-azabenzotriazol-1-yl)uronium hexafluorophosphate (HATU) or 1-(3-dimethylaminopropyl)-3-ethylcarbodiimide (EDC). The reaction is typically conducted at a temperature in the range of about 25° C. to about 100° C. for about 2 hours to about 16 hours, or until the reaction is substantially complete.

Compounds of the invention in which $R^2$ is —C(O)NHR$^4$, —C(O)OR$^5$, or S(O)$_2$R$^6$ may be prepared by similar processes using reagents $R^4$—N=C=O, $R^5$OC(O)-L' and $R^6$—S(O)$_2$-L', respectively, where L' represents a halo leaving group, in place of $R^{9a}$C(O)-L.

A general procedure for the preparation of an intermediate of formula (II) is illustrated in Scheme B

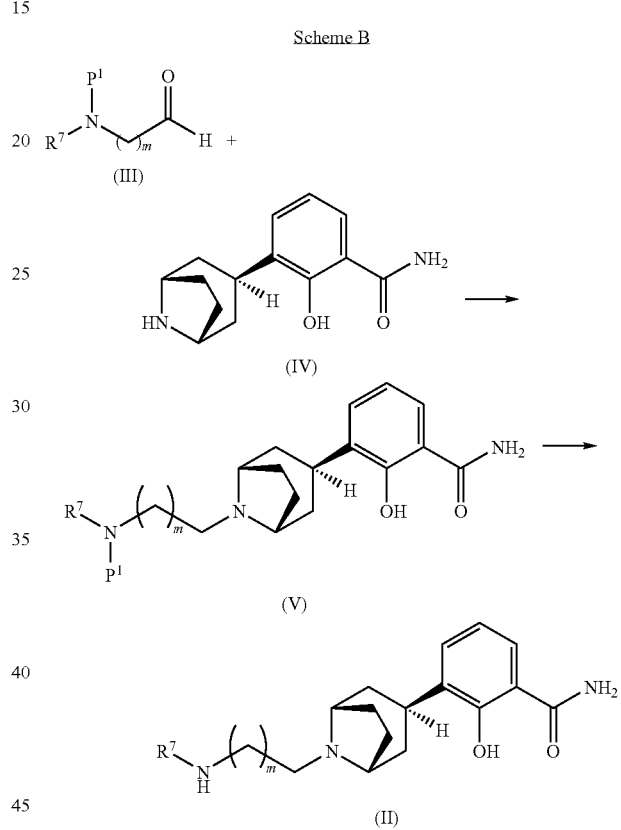

where $P^1$ represents an amino-protecting group. In Scheme B, intermediate (IV) is reductively N-alkylated by reaction with the aldehyde (III) to provide protected intermediate (V). The reaction is typically conducted by contacting intermediate (IV) with between about 1 and about 2 equivalents of an aldehyde of formula (III) in a suitable inert diluent, such as dichloromethane, in the presence of between about 0.9 and about 2 equivalents of a reducing agent. The reaction is typically conducted at a temperature in the range of about 0° C. to ambient temperature for about a half hour to about 3 hours or until the reaction is substantially complete. Typical reducing agents include sodium triacetoxyborohydride, sodium borohydride, and sodium cyanoborohydride. The product (V) is isolated by conventional means. The deprotection of (V) uses standard procedures. For example, when the protecting group $P^1$ is Boc, (V) is typically treated with an acid, such as trifluoroacetic acid to provide intermediate (II). When the protecting group is benzyloxycarbonyl (Cbz), (V) may be deprotected by catalytic hydrogenation, with, for example, a palladium hydroxide on carbon catalyst.

An exemplary process for the preparation of intermediates of formula (III') where R⁷ is —CH₂—R¹ is illustrated in Scheme C:

Scheme C

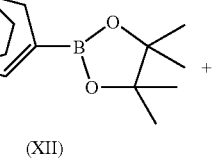

(VI)

(VII)

(III')

where all the variables take the values defined above. First, an amino-protecting group is added to intermediate (VI) by conventional procedures to form intermediate (VII), which is oxidized, for example, in the presence of a sulfur trioxide pyrdium complex, to provide an intermediate of formula (III').

The 8-azabicyclooctyl-2-hydroxybenzamide intermediate (IV) may be prepared by the Suzuki coupling of the bicyclic vinyl boronate (XII) with the benzyloxy-bromo-benzamide (X) as shown in step (c) of Scheme D below.

Scheme D (a)

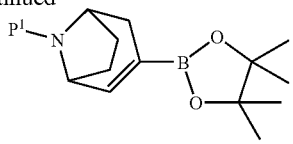

(VIII)   (IX)

(X)

(b)

(XI)

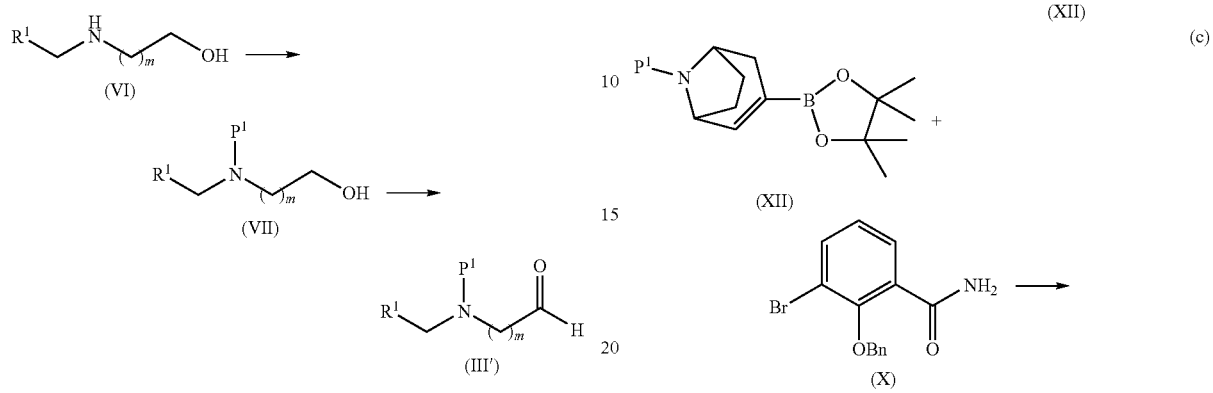

(XII)

(c)

(XII)

(X)

(XIII)

(IV)

The benzamide intermediate (X) may be prepared from 3-bromo-2-fluoro-benzonitrile (VIII) by the route shown in step (a) in which (VIII) is first converted to intermediate (IX), where Bn denotes the protecting group benzyl, by reaction with benzyl alcohol. The nitrile (IX) is then hydrolyzed to the corresponding amide to provide intermediate (X). The hydrolysis reaction may be performed by contacting (IX) with an excess of water in the presence of a platinum dialkylphosphonite catalyst, commonly termed Parkin's catalyst. The reaction is typically performed at reflux temperature for about 2 to about 20 hours or until the reaction is substantially complete.

The bicyclic vinyl boronate (XII) may be prepared by reaction of the protected bicyclooctene intermediate (XI), where P¹ represents an amino-protecting group, typically Boc or benzyl, and —OTf represents trifluoromethane sulfonate (commonly triflate) with bis(pinacolato)diboron as shown in step (b). The reaction is typically conducted by contacting (XII) with between about 1 and about 1.2 equivalents of bis(pinacolato)diboron in the presence of a catalytic amount of a palladium catalyst and a phosphine ligand, for example [1,1'-bis(diphenylphosphino)ferrocene]dichloropalladium (II) (Pd(dppf)Cl₂) and 1,1'-bis(diphenylphosphino)ferrocene (dppf). The reaction is typically conducted at a temperature between about 40 and about 80° C. for between about 4 and about 20 hours or until the reaction is substantially complete.

The protected bicyclooctene intermediate (XI) used in step (b), where P¹ is benzyl, is conveniently prepared from 8-benzyl-8-azabicyclo[3.2.1]octan-3-one:

by contacting the octanone with between about 1 and about 1.5 equivalents of N-phenyl-bis(trifluoromethanesulfonimide) and between about 1 and about 1.5 equivalents of a base, such as sodium bis(trimethylsilyl)amide. The reaction is typically conducted at a temperature between about −20 and about −10° C. for between about one half to about two hours, or until the reaction is substantially complete.

To prepare intermediate (XI) in which $P^1$ is Boc, the benzyl-protected octanone is first converted to the Boc-protected form by reaction with di-tert-butyl dicarbonate (commonly Boc$_2$O) and catalytic hydrogenation. The Boc-protected octanone is then reacted with N-phenyl-bis(trifluoromethanesulfonimide) and base as described above. The reaction of the Boc intermediate is typically conducted at a temperature, less than about −70° C., for between about 2 and about 5 hours, or until the reaction is substantially complete.

Finally, the bicyclic vinyl boronate (XII) and benzamide intermediate (X) are coupled to provide the protected intermediate (XIII), which is reduced and deprotected in one or more steps, to provide the 8-azabicyclooctyl-2-hydroxybenzamide intermediate (IV). The reaction is typically conducted by contacting (XII) with about 1 equivalent of intermediate (X) in the presence of a palladium catalyst, for example, bis(triphenylphosphine)-palladium(II) chloride (PdCl$_2$(PPh$_3$)$_2$). The reaction is typically conducted at reflux temperature for between about 4 and about 20 hours or until the reaction is substantially complete. When $P^1$ is Boc, typically, the Boc protecting group is first removed by conventional treatment with trifluoroacetic acid and then the bicyclooctene is simultaneously reduced and deprotected by palladium catalyzed hydrogenation. When a benzyl protecting group is used for $P^1$, the double bond reduction and removal of both benzyl groups can be accomplished in a single hydrogenation step.

An alternative process for the preparation of intermediate (IV) using Boc protected intermediate (XII') is illustrated in Scheme E:

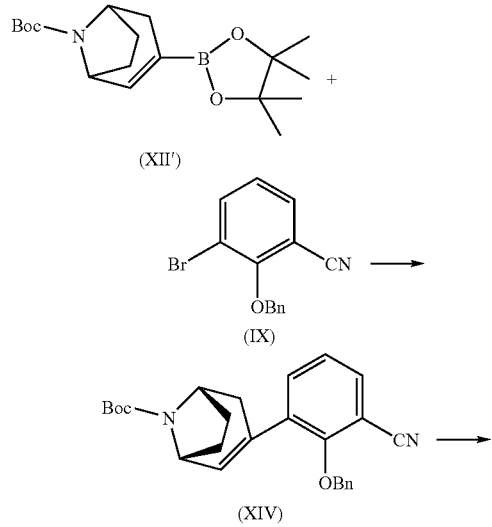

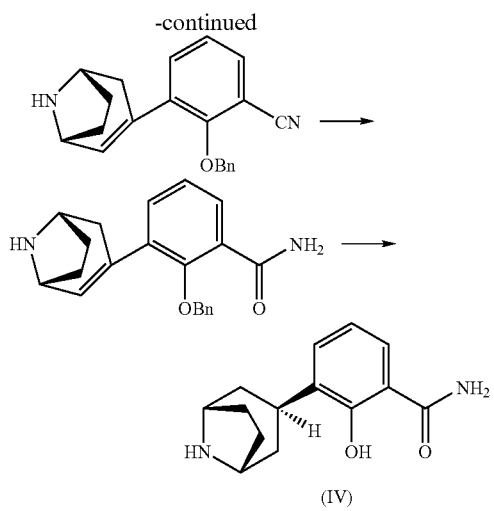

in which the order of the Suzuki coupling and the conversion of the nitrile to the amide is reversed. As shown in Scheme E, and described in the examples below, the 2-benzyloxy-3-bromo-benzonitrile intermediate (IX) is coupled to the bicyclic boronate (XII') to form nitrile intermediate (XIV). In subsequent steps, the Boc group is deprotected from the nitrile intermediate, the cyano group is hydrolyzed, and finally the double bond is reduced and the benzyl protecting group is removed to form the 2-hydroxybenzamide (IV).

Yet another alternative process for the preparation of intermediate (IV) is illustrated in Scheme F:

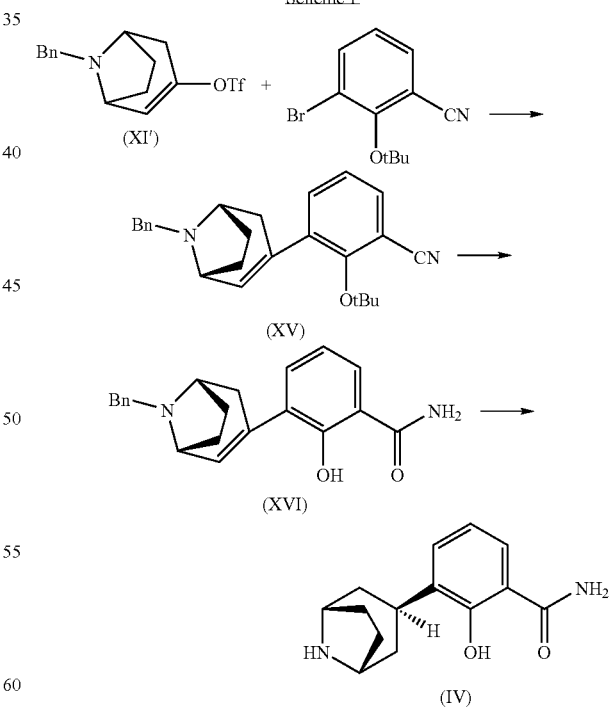

First, the benzyl-protected bicyclooctene intermediate (XI') is reacted with 2-butoxy-3-bromo-benzonitrile, the butoxy analog of intermediate (IX) to form the nitrite intermediate (XV). The reaction is typically conducted by contacting intermediate (XI') with between about 1 and about 1.5 equivalents of 2-butoxy-3-bromo-benzonitrile in an inert diluent, such as tetrahydrofuran, in the presence of between about 1 and about 1.5 equivalents of isopropylmagnesium chloride and a transition metal catalyst. The reaction is typically performed at reflux temperature for about one-half to about three hours or until the reaction is substantially complete. Intermediate (XV) is refluxed in an acidic solution to simultaneously hydrolyze the cyano group to the amide and remove the tert-butyl hydroxy-protecting group to provide intermediate (XVI). Finally, (XVI) is converted to the benzamide product (IV), in a single step, by reaction with between about 10 and about 15 equivalents of ammonium formate, in the presence of a palladium catalyst, which simultaneously reduces the bicyclooctene and removes the benzyl amino-protecting group.

Further details regarding specific reaction conditions and other procedures for preparing representative compounds of the invention or intermediates thereto are described in the examples below.

Accordingly, in a method aspect, the invention provides a process for preparing a compound of formula (Id), or a salt or protected derivative thereof, the process comprising reacting a compound of formula (II) with a compound of formula $R^{9a}C(O)$-L, and optionally removing a protecting group, to provide a compound of formula (Id), or a salt or protected derivative thereof.

In an additional aspect, the invention provides a compound of formula (II) and a compound of formula (IV), wherein the variables $R^7$ and m take any of the values described in aspects of the invention disclosed above.

Pharmaceutical Compositions

The 8-azabicyclooctane-2-hydroxybenzamide compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired. When discussing compositions, the "compound of the invention" may also be referred to herein as the "active agent". As used herein, the term "compound of the invention" is intended to include compounds of formula (I) as well as the species embodied in formulas (Ia), (Ib), (Ic), and (Id). "Compound of the invention" includes, in addition, pharmaceutically-acceptable salts and solvates of the compound unless otherwise indicated.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the compounds of the present invention may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide, 1-isopropyl-2- oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, and 4-(4-{[(2-isopropyl-1H-benzoimidazole-4-carbonyl)amino]methyl}-piperidin-1-ylmethyl)piperidine-1-carboxylic acid methyl ester and pharmaceutically-acceptable salts thereof may be used as the second therapeutic agent.

Additional useful prokinetic agents and other agents for gastrointestinal disorders include, but are not limited to, 5-HT$_3$ receptor agonists (e.g. pumosetrag), 5-HT$_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic M$_1$ and M$_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the compounds of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 µg/day to about 100 mg/day.

Accordingly, the pharmaceutical compositions of the invention optionally include a second therapeutic agent as described above.

The following examples illustrate representative pharmaceutical compositions of the present invention:

FORMULATION EXAMPLE A

Hard Gelatin Capsules for Oral Administration

A compound of the invention (50 g), spray-dried lactose (200 g) and magnesium stearate (10 g) are thoroughly blended. The resulting composition is loaded into a hard gelatin capsule (260 mg of composition per capsule).

FORMULATION EXAMPLE B

Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

FORMULATION EXAMPLE C

Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

FORMULATION EXAMPLE D

Tablets for Oral Administration

A compound of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

FORMULATION EXAMPLE E

Tablets for Oral Administration

A compound of the invention (25 mg), microcrystalline cellulose (400 mg), fumed silicon dioxide (10 mg), and stearic acid (5 mg) are thoroughly blended and then compressed to form tablets (440 mg of composition per tablet).

FORMULATION EXAMPLE F

Single-Scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

FORMULATION EXAMPLE G

Suspension for Oral Administration

The following ingredients are thoroughly mixed to form a suspension for oral administration containing 100 mg of active ingredient per 10 mL of suspension:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

FORMULATION EXAMPLE H

Dry Powder Composition

A micronized compound of the invention (1 mg) is blended with lactose (25 mg) and then loaded into a gelatin inhalation cartridge. The contents of the cartridge are administered using a powder inhaler.

FORMULATION EXAMPLE J

Injectable Formulation

A compound of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of the compounds of the invention, (i.e. free base, pharmaceutical salt, or solvate) that is suitable for the particular mode of administration, can be used in the pharmaceutical compositions discussed above.

Utility

The 8-azabicyclooctane compounds of the invention are antagonists at the mu opioid receptor and therefore are expected to be useful for treating medical conditions mediated by mu opioid receptors or associated with mu opioid receptor activity, i.e. medical conditions which are ameliorated by treatment with a mu opioid receptor antagonist. In particular, the compounds of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The mu opioid receptor antagonists of the invention are also expected to be useful for treating post-operative ileus, a disorder of reduced motility of the gastrointestinal tract that occurs after abdominal or other surgery. In addition, it has been suggested that mu opioid receptor antagonist compounds may be used for reversing opioid-induced nausea and vomiting. Further, those mu opioid receptor antagonists exhibiting some central penetration may be useful in the treatment of dependency on, or addiction to, narcotic drugs, alcohol, or gambling, or in preventing, treating, and/or ameliorating obesity.

Since compounds of the invention increase motility of the gastrointestinal (GI) tract in animal models, the compounds are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by mu opioid receptors, the compounds of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

As described above, compounds of the invention are mu opioid receptor antagonists. The invention further provides, therefore, a method of antagonizing a mu opioid receptor in a mammal, the method comprising administering a compound of the invention to the mammal.

The mu opioid receptor antagonists of the invention are optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

In addition, the compounds of the invention are also useful as research tools for investigating or studying biological systems or samples having mu opioid receptors, or for discovering new compounds having mu opioid receptor activity. Any suitable biological system or sample having mu opioid receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of contacting a biological system or sample comprising a mu opioid receptor with a compound of the invention are determined using conventional procedures and equipment, such as the radioligand binding assay and functional assay described herein or other functional assays known in the art. Such functional assays include, but are not limited to, ligand-mediated changes in intracellular cyclic adenosine monophosphate (cAMP), ligand-mediated changes in activity of the enzyme adenylyl cyclase, ligand-mediated changes in incorporation of analogs of guanosine triphosphate (GTP), such as [$^{35}$S] GTPγS (guanosine 5'-O-(γ-thio)triphosphate) or GTP-Eu, into isolated membranes via receptor catalyzed exchange of GTP analogs for GDP analogs, and ligand-mediated changes in free intracellular calcium ions. A suitable concentration of a compound of the invention for such studies typically ranges from about 1 nanomolar to about 500 nanomolar.

When using compounds of the invention as research tools for discovering new compounds have mu opioid receptor activity, binding or functional data for a test compound or a group of test compounds is compared to the mu opioid receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to exhibit potent binding to mu opioid receptors and little or no agonism in mu receptor functional assays. Therefore, the compounds of the invention are potent mu opioid receptor antagonists. Further, compounds of the invention have demonstrated predominantly peripheral activity as compared with central nervous system activity in animal models. Therefore, these compounds can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

AcOH=acetic acid
Boc=tert-butoxycarbonyl
$(Boc)_2O$=di-tert-butyl dicarbonate
DCM=dichloromethane
DIPEA=N,N-diisopropylethylamine
DMF=N,N-dimethylformamide
DMSO=dimethyl sulfoxide
EtOAc=ethyl acetate
EtOH=ethanol
HATU=N,N,N',N'-tetramethyl-O-(7-azabenzotriazol-1-yl)uronium hexafluorophosphate
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

Preparation 1: 2-Benzyloxy-3-bromobenzonitrile

To a flask containing sodium hydride (1.44 g, 60.0 mmol) suspended in DMF (60 mL, 800 mmol) at 0° C. was added benzyl alcohol (6.21 mL, 60.0 mmol) over 5 min. The reaction mixture was stirred at 0° C. for 30 min and then 3-bromo-2-fluorobenzonitrile (10.0 g, 50.0 mmol) in DMF (20 mL) was added. The reaction mixture was warmed to room temperature and stirred at 80° C. for 2 h, cooled to room temperature, and extracted with ethyl acetate (150 mL) and water (150 mL) The organic layer was washed with water (150 mL) and brine (150 mL), collected, dried over anhydrous sodium sulfate, filtered, and concentrated. The crude product was suspended with ethyl acetate:hexanes (1:3; 50 mL). The resulting suspension was stirred vigorously for 1 h, filtered, and dried. The mother liquor was concentrated and recrystallized. The crystals were combined and dried under vacuum to give the title compound (10.3 g).
$^1$H NMR (DMSO-$d_6$, 300 MHz) δ (ppm): 8.04 (dd, J=1.6, 8.2 Hz, 1H), 7.87 (dd, J=1.6, 7.6 Hz, 1H), 7.56-7.51 (m, 2H), 7.47-7.37 (m, 3H), 7.29 (t, J=7.9 Hz, 1H), 5.20 (s, 1H).

Preparation 2: 2-Benzyloxy-3-bromobenzamide

The product of Preparation 1 (10.3 g, 0.0357 mol) was dissolved in ethanol (20 mL, 0.4 mol), water (3.2 mL, 0.18 mol) and 1,4-dioxane (4 mL, 0.05 mol). hydrido(dimethylphosphoniousacid-kP)[hydrogen bis(dimethylphosphinito-kP)]platinum(II) (30 mg, 0.00007 mol) was added and the reaction mixture was heated to reflux overnight. To the hot solution was added water (~25 mL). The reaction mixture was cooled to room temperature. The resulting crystals were filtered, dissolved in ethyl acetate, dried with sodium sulfate, filtered, and evaporated to give a solid (9.1 g). The initial filtrate was evaporated to ~30 mL and cooled at 0° C. for 2 h. The resulting crystals were filtered and dried to provide additional product (1.65 g). $^1$H NMR (DMSO-$d_6$, 300 MHz) δ (ppm): 7.79 (br, 1H) 7.71 (dd, J=1.6, 8.0 Hz, 1H), 7.62 (br, 1H), 7.52-7.46 (m, 3H), 7.40-7.30 (m, 3H), 7.29 (t, J=7.8 Hz, 1H), 4.96 (s, 1H).

Preparation 3: 3-Trifluoromethanesulfonyloxy-8-azabicyclo[3.2.1]oct-2-ene-8-carboxylic acid tert-butyl ester A solution of 3-oxo-8-azabicyclo[3.2.1]octane-8-carboxylic acid tert-butyl ester (15.8 g, 70.0 mmol) and THF (150 mL) was cooled to −78° C. and 1.0 M sodium hexamethyldisilazane in THF (84 mL) was added dropwise over 5 min. The reaction mixture was stirred for 1 h and then N-phenylbis(trifluoromethane-sulphonimide) (25.0 g, 70.0 mmol) was added and the reaction mixture was stirred for 1 h. The solution was warmed to room temperature, 1.0 N NaOH (100 mL) was added, and the reaction mixture was stirred for 15 min. Approximately 75 mL of solvent was evaporated. The resulting solution was diluted with ethyl acetate:hexanes (100 mL:100 mL) and water (100 mL), extracted and washed with 1.0 N NaOH (2×200 mL). The organic layer was washed with saturated NaCl solution (200 mL). The organic layer was collected, dried over anhydrous sodium sulfate, filtered, and concentrated to give the title compound (18.2 g) as a dark oil, which was used without further purification.

Preparation 4: 3-(4,4,5,5-Tetramethyl-1,3,2-dioxaborolan-2-yl)-8-aza-bicyclo[3.2.1]oct-2-ene-8-carboxylic acid tert-butyl ester The product of Preparation 3 (7.65 g, 0.0214 mol) was dissolved in 1,4-dioxane (75 mL, 0.96 mol). To the reaction mixture was added bis(pinacolato)diboron (5.71 g, 0.0225 mol), and potassium acetate (6.30 g, 0.0642 mol), 1,1'-bis(diphenylphosphino)-ferrocene (0.5 g, 0.8 mmol) and [1,1'-bis(diphenylphosphino)ferrocene]-dichloropalladium(II), complex with dichloromethane (1:1) (0.5 g, 0.6 mmol). The reaction mixture was purged with nitrogen, stirred at 80° C. overnight, and cooled to room temperature. The solution was filtered through Celite and concentrated. The crude product was purified by flash column chromatography eluting with (5-10%) ethyl acetate in hexanes to give the title compound (4.2 g) as an oil.

Preparation 5: 3-endo-(8-Azabicyclo[3.2.1]oct-3-yl)-2-hydroxybenzamide a. 3-(8-Azabicyclo[3.2.1]oct-2-en-3-yl)-2-benzyloxybenzamide (A) and 3-(8-azabicyclo[3.2.1]oct-2-en-3-yl)-2-hydroxybenzamide (B)

To a flask was added 2-benzyloxy-3-bromobenzamide (1.60 g, 5.23 mmol), 3-(4,4,5,5-tetramethyl-1,3,2-dioxaborolan-2-yl)-8-azabicyclo[3.2.1]oct-2-ene-8-carboxylic acid tert-butyl ester (1.75 g, 5.23 mmol), THF (30 mL), 2.0 M sodium carbonate in water (10.4 mL), and bis(triphenylphosphine)palladium(II) chloride (92 mg, 0.13 mmol). The resulting mixture was purged with nitrogen, heated to reflux overnight, and cooled to room temperature. The reaction mixture was then concentrated, diluted with DCM (25 mL) and washed with water (25 mL) The organic layer was collected, dried over anhydrous sodium sulfate, filtered, and concentrated. To the reaction mixture was added DCM (10 mL) and TFA (10 mL) and the mixture was stirred at room temperature for 1 h, concentrated, and purified by preparative HPLC to give a mixture of the title compounds as their TFA salts. (A): (m/z): [M+H]$^+$ calcd for $C_{21}H_{22}N_2O_2$, 335.17; found 336.0; (B): (m/z): [M+H]$^+$ calcd for $C_{14}H_{16}N_2O_2$, 245.12; found 245.6.

b. 3-endo-(8-Azabicyclo[3.2.1]oct-3-yl)-2-hydroxybenzamide

To a flask under an atmosphere of nitrogen was added 10% Pd/C (0.1:0.9, palladium:carbon black, 0.040 g). The product of the previous step, 3-(8-aza -bicyclo[3.2.1]oct-2-en-3-yl)-2-benzyloxybenzamide TFA salt (0.400 g, 0.892 mmol) and 3-(8-azabicyclo[3.2.1]oct-2-en-3-yl)-2-hydroxybenzamide TFA salt (0.220 g, 0.614 mmol) in methanol (10 mL) was added and the reaction mixture was stirred under an atmosphere of hydrogen overnight, filtered through Celite, concentrated, and purified by preparative HPLC to provide the title compound as its TFA salt (0.346 g). (m/z): [M+H]$^+$ calcd for $C_{14}H_{18}N_2O_2$, 247.14; found 247.2.

Preparation 6: 3-endo-(8-Azabicyclo[3.2.1]oct-3-yl)-2-hydroxybenzamide a. 3-(2-Benzyloxy-3-cyanophenyl)-8-aza-bicyclo[3.2.1]oct-2-ene-8-carboxylic acid tert-butyl ester To a flask was added 2-benzyloxy-3-bromobenzonitrile (1.29 g, 4.47 mmol), 3-(4,4,5,5-tetramethyl-1,3,2-dioxaborolan-2-yl)-8-azabicyclo[3.2.1]oct-2-ene-8-carboxylic acid tert-butyl ester (1.50 g, 4.47 mmol), and THF (30 mL), 2.0 M sodium carbonate in water (8.95 mL), and bis(triphenylphosphine)palladium(II) chloride (78 mg, 0.11 mmol). The reaction mixture was purged with nitrogen, heated to reflux overnight, cooled to room temperature, and concentrated. The resulting solution was diluted with DCM (25 mL) and washed with water (25 mL) The organic layer was collected, dried over anhydrous sodium sulfate, filtered, and concentrated. The crude product was purified by flash column chromatography eluting with ethyl acetate in hexanes (0-50%) to give partially purified product (1.2 g). (m/z): [M+H]$^+$ calcd for $C_{26}H_{28}N_2O_3$ 416.21; (-tert-butyl 361.2); found 361; (-Boc 317.2); found 317.

b. 3-(8-Azabicyclo[3.2.1]oct-2-en-3-yl)-2-benzyloxybenzamide

To the product of the previous step (1.20 g, 0.00287 mol) in DCM (10 mL) was added TFA (10 mL). The reaction mixture was stirred for 1 h, concentrated, diluted with ethanol (2×20 mL), and concentrated. Ethanol (10 mL) and water (4 mL) were added followed by hydrido(dimethylphosphonious acid-kP)[hydrogen bis(dimethylphosphinito-kP)]platinum (II) (20 mg, 0.05 mmol). The reaction mixture was heated at 75° C. overnight, cooled to room temperature, concentrated, and purified by preparative HPLC to give the title compound as its TFA salt (0.520 g). (m/z): [M+H]$^+$ calcd for $C_{21}H_{22}N_2O_2$, 335.17; found 336.0.

c. 3-endo-(8-Azabicyclo[3.2.1]oct-3-yl)-2-hydroxybenzamide

To a flask under an atmosphere of nitrogen was added 10% Pd/C (0.1:0.9, palladium:carbon black, 0.050 g). The product of the previous step (0.520 g, 1.16 mmol) was added and the reaction mixture was stirred under an atmosphere of hydrogen overnight, filtered through Celite, concentrated, and purified by preparative HPLC to provide the title compound as its TFA salt (0.310 g). (m/z): [M+H]$^+$ calcd for $C_{14}H_{18}N_2O_2$, 247.14; found 247.2.

Preparation 7: 3-endo-(8-Azabicyclo[3.2.1]oct-3-yl)-2-hydroxybenzamide a. 8-Benzyl-3-(4,4,5,5-tetramethyl-1,3,2-dioxaborolan-2-yl)-8-azabicyclo[3.2.1]oct-2-ene Trifluoro-methanesulfonic acid 8-benzyl-8-azabicyclo[3.2.1]oct-2-en-3-yl ester (13.2 g, 0.0380 mol) was dissolved in 1,4-dioxane (200 mL, 2 mol) and bis(pinacolato)diboron (10.1 g, 0.0399 mol), potassium acetate (11.2 g, 0.114 mol), 1,1'-bis(diphenylphosphino)ferrocene (0.8 g, 0.002 mol) and [1,1'-bis(diphenylphosphino)ferrocene]dichloropalladium (II) complex with dichloromethane (1:1) (0.9 g, 0.001 mol) was added. The reaction mixture was purged with nitrogen and stirred at 80° C. overnight. The reaction mixture was cooled to room temperature, filtered through Celite, concentrated, and purified by flash column chromatography eluting with dichloromethane to give the title intermediate as a brown oil (6.0 g).

b. 8-Benzyl-8-azabicyclo[3.2.1]oct-2-en-3-yl)-2-benzyloxybenzamide

To a flask was added 2-benzyloxy-3-bromobenzamide (3.8 g, 12 mmol), the product of the previous step (4.0 g, 12 mmol), THF (80 mL) and 2.0 M sodium carbonate in water (24.6 mL) followed by bis(triphenylphosphine)palladium(II) chloride (220 mg, 0.31 mmol). The reaction mixture was purged with nitrogen and heated to reflux overnight. The reaction mixture was cooled to room temperature, concentrated, diluted with ethyl acetate (50 mL) and washed with water (50 mL). The organic layer was collected, dried over anhydrous sodium sulfate, filtered, concentrated, and purified by flash column chromatography eluting with dichloromethane:methanol (1% to 4% gradient with 0.5% triethylamine) to give partially purified product (5.1 g). (m/z): $[M+H]^+$ calcd for $C_{28}H_{28}N_2O_2$, 445.22; found 445.2.

c. 3-endo-(8-Azabicyclo[3.2.1]oct-3-yl)-2-hydroxybenzamide

To a flask under an atmosphere of nitrogen was added Pearlman's Catalyst (0.1:0.4, palladium hydroxide:carbon black, 0.500 g) and then the product of the previous step (4.0 g, 0.0094 mol) and trifluoroacetic acid (0.92 mL) in methanol (40 mL). The reaction mixture was stirred under hydrogen (30 psi) overnight, filtered through Celite, concentrated and purified by preparative HPLC to give the title compound as its TFA salt. (530 mg) and 3-exo-(8-azabicyclo[3.2.1]oct-3-yl)-2-hydroxybenzamide (90 mg). (m/z): $[M+H]^+$ calcd for $C_{14}H_{18}N_2O_2$, 247.14; found 247.2.

Preparation 8: 3-endo-(8-[2-(2-Ethylbutylamino)ethyl]-8-azabicyclo[3.2.1]oct-3-yl-2-hydroxybenzamide a. 2-(2-Ethylbutylamino)ethanol

A mixture of 3-bromomethyl-pentane (6.0 g, 36.4 mmol) and ethanolamine (13 mL, 218 mmol) in ethanol (45 mL) was heated at 75° C. for 16 h. The reaction mixture was concentrated and the resulting residue was diluted with DCM (70 mL). The organic layer was partitioned with water (70 mL) and the aqueous layer extracted with DCM. Combined organic layers, dried over magnesium sulfate, filtered, and concentrated to give the title compound as an oil (4.90 g). $^1$H NMR (d6-DMSO, 400 MHz) δ (ppm): 3.44 (t, J=5.6 Hz, 2H), 2.54 (t, J=6.0 Hz, 2H), 2.40 (d, J=5.6 Hz, 2H), 1.31-1.25 (m, 5H), 0.83 (t, J=6.8 Hz, 6H).

b. (2-Ethylbutyl)-(2-hydroxyethyl)-carbamic acid tert-butyl ester

To the solution of the product of the previous step (3.0 g, 20.7 mmol) in DCM (30 mL) at 0° C. was added a solution of di-tert-butyl dicarbonate (4.06 g, 18.6 mmol) dropwise over 5 min. The resulting mixture was warmed to room temperature and stirred overnight under an atmosphere of nitrogen. The crude reaction mixture was diluted with DCM (50 mL) and washed successively with 1 N aq HCl (2×50 mL), saturated $NaHCO_3$ (2×50 mL) and brine 2×50 mL). The organic layer was dried over magnesium sulfate, filtered, and concentrated to yield the title compound (5.4 g). $^1$H NMR ($d_6$-DMSO, 400 MHz) δ (ppm): 4.62 (br s, 1H) 3.44 (t, J=6.0 Hz, 2H), 3.2 (m, 2H), 3.09 (d, J=7.2 Hz, 2H), 1.50 (m, overlap with solvent, 1H), 1.38 (s, 9H), 1.25-1.87 (m, 4H), 0.83 (t, J=7.2 Hz, 6H).

c. (2-Ethylbutyl)-(2-oxoethyl)carbamic acid tert-butyl ester

To a solution of the product of the previous step (3.4 g, 13.9 mmol) in DCM (20 mL) at 0° C. was added sequentially DMSO (1.63 g, 20.9 mmol), DIPEA (4.48 g, 34.7 mmol) and sulfur trioxide pyridium complex (5.5 g, 34.7 mmol). The reaction mixture was stirred for 16 h, diluted with DCM (20 mL) and washed successively with 1N aqueous HCl (50 mL), saturated $NaHCO_3$ (50 mL) and brine (50 mL). The organic layer was dried over magnesium sulfate, filtered, and concentrated. The crude material was filtered through silica gel and eluted with DCM. After concentration, the title compound was obtained as a dark orange oil (2.34 g). (m/z): $[M+H]^+$ calcd for $C_{13}H_{25}NO_3$, 244.18; found, 244.0.

d. 2-[3-endo-(3-Carbamoyl-2-hydroxyphenyl)-8-azabicyclo[3.2.1]oct-8-yl]-ethyl-(2-ethylbutyl)-carbamic acid tert-butyl ester To a flask were added 3-endo-(8-azabicyclo[3.2.1]oct-3-yl)-2-hydroxybenzamide TFA salt (0.260 g, 0.722 mmol), (2-ethylbutyl)-(2-oxoethyl)carbamic acid tert-butyl ester (0.211 g, 0.866 mmol), and DIPEA (126 μL, 0.72 mmol) in DCM (8.7 mL) followed by sodium triacetoxyborohydride (0.184 g, 0.866 mmol). The reaction mixture was concentrated and purified by preparative HPLC to provide the title compound as its TFA salt (0.360 g). (m/z): $[M+H]^+$ calcd for $C_{27}H_{43}N_3O_4$, 474.33; found 474.4.

e. 3-endo-(8-[2-(2-Ethylbutylamino)ethyl]-8-azabicyclo[3.2.1]oct-3-yl-2-hydroxybenzamide The product of the previous step (0.360 g, 0.760 mmol) was dissolved in DCM (10 mL). Trifluoroacetic acid (10 mL) was added and the reaction mixture was stirred for 2 h, concentrated, and dissolved in water (5 mL) and acetonitrile (5 g). The resulting solution was frozen and lyophilized to give the title compound (220 mg) which was used without further purification. (m/z): $[M+H]^+$ calcd for $C_{22}H_{35}N_3O_2$, 374.27; found 373.8.

Preparation 9: 3-endo-(8-2-[(4,4-Difluorocyclohexylmethyl)amino]-ethyl-8-azabicyclo[3.2.1]oct-3-yl)-2-hydroxybenzamide a. (4,4-Difluorocyclohexyl)methanol

To a reaction mixture of 4,4-difluorocyclohexanecarboxylic acid ethyl ester (7.1 g, 37 mmol) in THF (50 mL) cooled to 0° C. was added dropwise 2.0 M lithium tetrahydroaluminate in THF (18.5 mL) over 10 min. The reaction mixture was stirred at 0° C. for 1 h. Water (5 mL) was added dropwise, followed by 1.0N NaOH (5 mL). The reaction mixture was filtered through Celite, THF was evaporated, and the resulting aqueous solution was diluted with brine (50 mL) and extracted with ethyl acetate (50 mL). The organic layer was collected, dried over anhydrous sodium sulfate, filtered, and concentrated to give the title compound as a clear oil (5.6 g) which was used without further purification.

b. Methanesulfonic acid 4,4-difluorocyclohexylmethyl ester

To the product of the previous step (5.5 g, 0.037 mol) and triethylenediamine (4.11 g, 0.0366 mol) in DCM (50 mL) cooled to 0° C. was added dropwise methanesulfonyl chloride (3.12 mL, 0.0403 mol). The reaction mixture was stirred at 0° C. for 30 min, warmed to room temperature, and washed with water (100 mL). The organic layer was collected, dried over anhydrous sodium sulfate, filtered, and concentrated to give the title compound as a white solid (8.5 g) which was used without further purification.

c. 2-[(4,4-Difluorocyclohexylmethyl)amino]ethanol

A solution of the product of the previous step (8.4 g, 0.037 mol) and ethanolamine (20 mL, 0.4 mol) in ethanol (20 mL) was stirred at 65° C. overnight. The reaction mixture was concentrated, and extracted with ethyl acetate (50 mL) and water (150 mL). The organic layer was washed with water (100 mL) and then with brine (50 mL). The organic layer was collected, dried over anhydrous sodium sulfate, filtered, and concentrated to give the title compound (3.3 g).

d. (4,4-Difluorocyclohexylmethyl)-(2-hydroxyethyl) carbamic acid tert-butyl ester To a solution of the product of the previous step (3.0 g, 16 mmol) and DIPEA (2.70 mL) in DCM (80 mL) was added dropwise di-tert-butyldicarbonate (2.7 g, 12 mmol) in DCM (20 mL). The reaction mixture was stirred for 1 h, washed with 0.1N HCl (150 mL), and then washed with water (100 mL) The organic layer was collected, dried over anhydrous sodium sulfate, filtered, and concentrated to give the title compound as a yellow oil (4.0 g).

e. (4,4-Difluorocyclohexylmethyl)-(2-oxoethyl)-carbamic acid tert-butyl ester To a solution of DIPEA (4.75 mL) and the product of the previous step (4.0 g, 0.0136 mol) in DCM (20 mL) cooled to −20° C. was added sulfur trioxide -pyridine complex (4.34 g, 0.0273 mol) in DMSO (20 g). The reaction mixture was stirred for 1 h and then DCM (50 mL) was added. The reaction mixture was washed with 10% AcOH in water (100 mL) and with water (100 mL). The organic layer was collected, dried over anhydrous sodium sulfate, filtered, and concentrated to give an oil. The crude product was purified by flash column chromatography eluting with 10 to 40% ethyl acetate in hexanes to give the title compound as an oil (2.8 g).

f. 3-endo-(8-2-[(4,4-Difluorocyclohexylmethyl) amino]-ethyl-8-azabicyclo[3.2.1]oct-3-yl)-2-hydroxybenzamide To a solution of 3-endo-(8-azabicyclo[3.2.1]oct-3-yl)-2-hydroxybenzamide TFA salt (0.10 g, 0.278 mmol) (Preparation 6), the product of the previous step (0.130 g, 0.447 mmol) and DIPEA (70.7 µL, 0.406 mmol) in DCM (5 mL) was added sodium triacetoxyborohydride (0.0946 g, 0.447 mmol) The reaction mixture was stirred for 1 h and then concentrated. DCM (5 mL) was added followed by trifluoroacetic acid (5 mL, 0.06 mol). The reaction mixture was stirred for 30 min, concentrated and purified by preparative HPLC to give the title compound as its TFA salt (0.102 g). (m/z): [M+H]$^+$ calcd for $C_{23}H_{33}F_2N_3O_2$, 422.25; found 422.0.

Preparation 10: 3-endo-(8-[2-(2,2-Dimethylpropylamino)ethyl]-8-aza-bicyclo[3.2.1]oct-3-yl)-2-hydroxybenzamide a. 2,2-Dimethylpropyl-(2-oxoethyl)-carbamic acid benzyl ester

To a solution of pivaldehyde (1.00 mL, 0.00921 mol) in DCM (30 mL) was added 2,2-diethoxy-ethanamine, (1.35 mL, 0.00921 mol) followed by sodium triacetoxyborohydride (2.15 g, 0.0101 mol). The reaction mixture was stirred at room temperature for 1 h and then DIPEA (1.43 g, 0.0110) mol) was added. The reaction mixture was cooled to 0° C., and benzyl chloroformate (1.88 g, 0.0110 mol) was added dropwise. The reaction mixture was stirred for 1 h, concentrated, and 6 M TFA in water (20 mL) was added. The reaction mixture was stirred for 2 h and the TFA was removed under vacuum. The resulting aqueous solution was diluted with saturated NaCl (15 mL) The product was extracted with ethyl acetate (25 mL). The organic layer was collected, dried over anhydrous sodium sulfate, filtered, and concentrated. The crude product was purified by flash column chromatography eluting with 10-20% ethyl acetate in hexanes to give an oil (2.2 g) which was further purified by flash column chromatography to give the title compound as a yellow oil (0.72 g).

b. 2-[3-endo-(3-Carbamoyl-2-hydroxyphenyl)-8-azabicyclo[3.2.1]oct-8-yl]-ethyl-(2,2-dimethyl-propyl)carbamic acid benzyl ester To a solution of 3-endo-(8-azabicyclo[3.2.1]oct-3-yl)-2-hydroxybenzamide TFA salt (0.10 g, 0.278 mmol) (Preparation 6), the product of the previous step (80.4 mg, 0.305 mmol) in DCM (5 mL, 0.08 mol) was added DIPEA (48.3 µL, 0.27 mmol) followed by sodium triacetoxyborohydride (70.6 mg, 0.333 mmol). The reaction mixture was stirred for 1 h, concentrated, and purified by preparative HPLC to give the title compound as its TFA salt (0.15 g). (m/z): [M+H]$^+$ calcd for $C_{29}H_{39}N_3O_4$, 494.29; found 494.6.

c. 3-endo-(8-[2-(2,2-Dimethylpropylamino)ethyl]-8-azabicyclo[3.2.1]oct-3-yl)-2-hydroxybenzamide To a solution of the product of the previous step (0.150 g, 0.247 mmol) in methanol (5 mL, 0.1 mol) was added 10% Pd/C (0.1:0.9, palladium:carbon black, 15 mg). The reaction mixture was stirred under an atmosphere of hydrogen for 2 h, filtered through Celite, and concentrated to give the title compound as a white solid (0.12 g). (m/z): [M+H]$^+$ calcd for $C_{22}H_{35}N_3O_2$, 360.26; found 360.4.

Preparation 11: 3-endo-(8-Azabicyclo[3.2.1]oct-3-yl)-2-hydroxybenzamide a. 3-Bromo-2-tert-butoxy-benzonitrile

A mixture of 3-bromo-2-fluoro-benzonitrile (40.0 g, 0.200 mol) and tetrahydrofuran (200 mL) was chilled to 0° C. and stirred for 5 min. A solution of potassium tert-butoxide (130 mL, 0.210 mol) was added dropwise at 0° C. and the reaction was allowed to warm to RT with stirring over 90 min. The reaction was quenched with water (200 mL) and 2 M $Na_2CO_3$ (100 mL) and extracted with EtOAc (3×200 mL). The organic layer was dried over $Na_2SO_4$ and the solvent was removed by rotary evaporation to provide the title compound as a light yellow oil.

b. 3-(8-Benzyl-8-aza-bicyclo[3.2.1]oct-2-en-3-yl)-2-tert-butoxy-benzonitrile To a solution of 3-bromo-2-tert-butoxy-benzonitrile (30.73 g, 0.121 mol) in THF (100 mL) at 0° C. was added 2 M isopropylmagnesium chloride in THF (60 mL) dropwise. The reaction mixture was stirred for 1 h and then tetrakis(triphenylphosphine)palladium(0) (2.33 g, 0.002 mol) was added followed by trifluoro-methanesulfonic acid 8-benzyl-8-azabicyclo[3.2.1]oct-2-en-3-yl ester (35.00 g, 0.101 mol) in THF (23 mL). The reaction mixture was refluxed at 80° C. for 1 h, cooled to RT, washed with brine, and extracted with EtOAc (2×). The organic layer was dried over sodium sulfate and the solvent was evaporated to provide the title compound (39.2 g) which was used without further purification. (m/z): [M+H]$^+$ calcd for $C_{25}H_{28}N_2O$ 373.22; found 373.2.

c. 3-(8-Benzyl-8-aza-bicyclo[3.2.1]oct-2-en-3-yl)-2-hydroxy-benzamide

Trifluoroacetic Acid (50 mL) and sulfuric acid (20 mL) were added to crude 3-(8-benzyl-8-aza-bicyclo[3.2.1]oct-2-en-3-yl)-2-tert-butoxy-benzonitrile (37.53 g, 0.101 mol) and the reaction mixture was heated at 65° C. overnight, poured into ice water and neutralized to pH 7. The aqueous layer was extracted EtOAc (3×) and the solvent was evaporated. The reaction mixture was purified by silica gel chromatography (10 min 7% MeOH:DCM, 10 min 10% MeOH:DCM, ramping to 20% MeOH:DCM over 30 min) to provide the title compound (22.15 g). (m/z): [M+H]$^+$ calcd for $C_{21}H_{22}N_2O_2$ 335.17; found 335.4 d. 3-endo-(8-Azabicyclo[3.2.1]oct-3-yl)-2-hydroxy-benzamide

Ethanol (1.23 L) was slowly added to palladium (6.15 g, 0.058 mol) (10% Pd, 50% water). The reaction mixture was stirred for 5 min, 3-(8-benzyl-8-aza-bicyclo[3.2.1]oct-2-en-3-yl)-2-hydroxy-benzamide (6.15 g, 0.018 mol) in EtOH (40 mL) was added, and then ammonium formate (12.30 g, 0.195 mol) was added slowly. The reaction mixture was heated at 60° C. for about 3 h and filtered through celite, washing with EtOH. The solvent was removed by rotary evaporation to provide the formic acid salt of the title compound (5.46 g). (m/z): [M+H]$^+$ calcd for $C_{14}H_{18}N_2O_2$ 247.14; found 247.4. $^1$H NMR (DMSO-d$_6$, 600 MHz) δ (ppm): 8.54 (s, 1H), 8.45 (s, 1H), 7.96 (s, 1H), 7.75 (d, J=7.8 Hz, 1H), 7.48 (d, J=7.32 Hz, 1H), 6.82 (t, J=7.64 Hz, 1H), 3.92 (s, 2H), 3.35 (m, 2H), 2.37 (m, 2H), 1.95 (m, 2H), 1.80 (m, 4H). Two-dimensional Nuclear Overhauser Effect Spectroscopy (NOESY) data was analyzed and found to be consistent with endo configuration.

Preparation 12: 3-endo-(8-2-[(4,4-Difluoro-cyclohexylmethyl)-amino]-ethyl-8-aza-bicyclo[3.2.1]oct-3-yl)-2-hydroxy-benzamide a. (4,4-Difluoro-cyclohexylmethyl)-(2-hydroxy-ethyl)-carbamic acid benzyl ester Benzyl chloroformate (4.8 mL, 33.2 mmol) was added to a solution of 2-[(4,4-difluoro-cyclohexylmethyl)-amino]-ethanol (6.41 g, 33.2 mmol) and DIPEA (5.8 mL) in DCM (200 mL) and the reaction mixture was stirred for 1 h. The reaction mixture was washed with 0.1 N HCl (150 mL) and then with water (100 mL). The organic layer was collected, dried over anhydrous sodium sulfate, filtered, and concentrated to give the title product as a clear oil (9.1 g) which partially crystallized overnight.

b. (4,4-Difluoro-cyclohexylmethyl)-(2-oxo-ethyl)-carbamic acid benzyl ester

A solution of DIPEA (9.68 mL, 0.056 mol) and the product of the previous step (9.1 g, 0.028 mol) in DCM (40 mL) was cooled at −20° C. and sulfur trioxide-pyridine complex (8.85 g, 0.056 mol) in dimethylsulfoxide (20 mL) was added. The reaction mixture was stirred for 1 h and DCM (50 mL) was added. The reaction mixture was washed with 10% AcOH in water (100 mL) and then with water (100 mL). The organic layer was collected, dried over anhydrous sodium sulfate, filtered, and concentrated to give an oil. The crude product was purified by silica gel chromatography eluting with 10-40% ethyl acetate in hexanes to give the title compound as an oil (6.3 g).

c. 2-[(3-endo-(3-Carbamoyl-2-hydroxy-phenyl)-8-aza-bicyclo[3.2.1]oct-8-yl]-ethyl-(4,4-difluoro-cyclohexylmethyl)-carbamic acid benzyl ester Sodium triacetoxyborohydride (142 mg, 0.67 mmol) was added to a solution of 3-endo-8-aza-bicyclo[3.2.1]oct-3-yl-2-hydroxy-benzamide TFA salt (220 mg, 0.61 mmol), (4,4-difluoro-cyclohexylmethyl)-(2-oxo-ethyl)-carbamic acid benzyl ester (218 mg, 0.67 mmol), and DIPEA (110 μL, 0.61 mmol) in DCM (10 mL). The reaction mixture was stirred for 1 h, concentrated, and was purified by preparative HPLC to give the TFA salt (0.260 g). The crude product was dissolved with DCM (10 mL) and washed with 1 M NaHCO$_3$ (10 mL). The organic layer was collected, dried over anhydrous sodium sulfate, filtered, and concentrated to give the title compound (215 mg). (m/z): [M+H]$^+$ calcd for $C_{31}H_{39}F_2N_3O_4$, 556.29; found 556.2.

d. 3-endo-(8-2-[(4,4-Difluoro-cyclohexylmethyl)-amino]-ethyl-8-aza-bicyclo[3.2.1]oct-3-yl)-2-hydroxy-benzamide The product of the previous step (215 mg, 0.39 mol) in methanol (10 mL) was added to palladium hydroxide (20 mg, 0.14 mmol). The reaction was stirred under an atmosphere of hydrogen overnight. The reaction was filtered through celite and concentrated to give the title compound (160 mg). (m/z): [M+H]$^+$ calcd for $C_{23}H_{33}F_2N_3O_2$, 422.25; found 422.2.

Preparation 13: 3-endo-[8-(3-Amino-propyl)-8-aza-bicyclo[3.2.1]oct-3-yl]-2-hydroxy-benzamide a. 3-endo-[3-(3-Carbamoyl-2-hydroxy-phenyl)-8-aza-bicyclo[3.2.1]oct-8-yl]-propyl-carbamic acid benzyl ester Sodium triacetoxyborohydride (249 mg, 1.17 mmol) was added to a mixture of 3-endo-8-aza-bicyclo[3.2.1]oct-3-yl-2-hydroxy-benzamide formic acid salt (286 mg, 0.98 mmol) and (3-oxo-propyl)-carbamic acid benzyl ester (223 mg, 1.08 mmol) in DMF (3 mL). The reaction mixture was stirred for 1 h, concentrated, and purified by preparative HPLC to give the title compound as its TFA salt (460 mg). (m/z): [M+H]$^+$ calcd for $C_{25}H_{31}N_3O_4$ 438.23; found 438.2.

b. 3-endo-[8-(3-Amino-propyl)-8-aza-bicyclo[3.2.1]oct-3-yl]-2-hydroxy-benzamide

To a solution of the product of the previous step (460 mg, 0.83 mmol) in methanol (10 mL) was added Pearlman's Catalyst, wet (0.1:0.4:0.5, palladium hydroxide:carbon black:water, 46 mg, 0.03 mmol). The reaction mixture was placed under an atmosphere of hydrogen and stirred overnight, filtered through celite, and concentrated to give the title compound as its TFA salt (310 mg). (m/z): [M+H]$^+$ calcd for $C_{17}H_{25}N_3O_2$ 304.19; found 304.2.

Preparation 14: 3-endo-8-[2-(Cyclohexylmethyl-amino)-ethyl]-8-aza-bicyclo[3.2.1]oct-3-yl-2-hydroxy-benzamide Sodium triacetoxyborohydride (453 mg, 2.14 mmol) was added to a mixture of cyclohexylmethyl-(2-oxo-ethyl)-carbamic acid benzyl ester (309 mg, 1.06 mmol), 3-endo-8-azabicyclo[3.2.1]oct-3-yl-2-hydroxy-benzamide formate (250 mg, 0.86 mmol) and DMF (5 mL). The reaction mixture was stirred for 2 h, and extracted with ethyl acetate (10 mL) and saturated NaHCO$_3$ (10 mL). The organic layer was collected, dried over anhydrous sodium sulfate, filtered, and concentrated. The resulting solid was dissolved with methanol (10 mL), and placed under an atmosphere of nitrogen. Pearlman's catalyst, wet (0.1:0.4:0.5, palladium hydroxide:carbon black:water, 0.25 mg) was added and the reaction mixture was stirred under an atmosphere of hydrogen overnight, filtered through celite, and concentrated, to provide the title intermediate which was used without further purification (270 mg). (m/z): [M+H]$^+$ calcd for $C_{23}H_{35}N_3O_2$ 386.27; found 386.6.

Example 1

3-endo-(8-{2-[((S)-2,3-Dihydroxypropionyl)-(2-ethylbutyl)-amino]ethyl}-8-azabicyclo[3.2.1]oct-3-yl)-2-hydroxybenzamide To a solution of 3-endo-(8-[2-(2-ethylbutylamino)ethyl]-8-azabicyclo[3.2.1]oct-3-yl-2-hydroxybenzamide TFA (20 mg, 0.033 mmol) (Preparation 8), lithium (S)-2,2-dimethyl-1,3-dioxolane-4-carboxylate (5.56 mg, 0.0366 mmol) and DIPEA (17 mL, 0.10 mmol) in DMF (0.3 mL) was added N,N,N',N'-tetramethyl-O-(7-azabenzotriazol-1-yl)uronium hexafluorophosphate (13.9 mg, 0.0366 mmol). The reaction mixture was stirred for 2 h and concentrated. Acetic acid (0.5 mL) and water (0.5 mL) were added and the reaction mixture was stirred at 75° C. overnight, cooled to room temperature, and purified by preparative HPLC to give the title compound as its TFA salt (8.0 mg). (m/z): [M+H]$^+$ calcd for $C_{25}H_{39}N_3O_5$ 462.29; found: 462.3. $^1$H NMR (CD$_3$OD 400 MHz) 7.7 (dd, 1H), 7.6 (d, 1H), 6.9 (t, 1H), 4.6 (t, 1H), 4.2 (m, 1H), 4.1-4.0 (m, 2H), 3.8 (3,2H), 3.7-3.6 (m, 1H), 3.6-3.3 (m, 3H), 3.3-3.2 (m, 2H), 2.8-2.6 (m, 2H), 2.4-2.2 (m, 4H), 2.2-2.0 (m, 2H), 1.7-1.6 (m, 1H), 1.5-1.3 (m, 4H), 1.1-0.9 (m, 6H).

Example 2

3-endo-(8-2-[(2-Ethylbutyl)-(2-hydroxyacetyl)amino]-ethyl -8-azabicyclo[3.2.1]oct-3-yl)-2-hydroxybenzamide To a solution of 3-endo-(8-[2-(2-ethylbutylamino)ethyl]-8-azabicyclo[3.2.1]oct-3-yl-2-hydroxybenzamide TFA (65 mg, 0.11 mmol) (Preparation 8) and DIPEA (22 μL, 0.13 mmol) in DCM (2 mL) was added acetoxyacetyl chloride (14 μL, 0.13 mmol). The reaction mixture was stirred for 1 h and concentrated. Methanol (5 mL) was added followed by 6 N NaOH (200 μL). The reaction mixture was stirred at room temperature for 1 h, concentrated, and purified by preparative HPLC to give the title compound as its TFA salt (33 mg). (m/z): [M+H]$^+$ calcd for $C_{24}H_{37}N_3O_4$ 432.28; found: 432.8.

Example 3

3-endo-(8-2-[(2-Ethylbutyl)-(2-methanesulfonylacetyl)amino]-ethyl-8-aza-bicyclo[3.2.1]oct-3-yl)-2-hydroxybenzamide To a solution of 3-endo-(8-[2-(2-ethylbutylamino)ethyl]-8-azabicyclo[3.2.1]oct-3-yl-2-hydroxybenzamide TFA (20 mg, 0.033 mmol) (Preparation 8), 1 methanesulfonyl-acetic acid (5.05 mg, 0.0366 mmol) and DIPEA (17 μL, 0.10 mmol) in DMF (10.3 mL) was added N,N,N',N'-tetramethyl-O-(7-azabenzotriazol-1-yl)uronium hexafluorophosphate (15 mg, 0.040 mmol). The reaction mixture was stirred for 2 h, concentrated, and purified by preparative HPLC to give the title compound as its TFA salt (8.8 mg). (m/z): [M+H]$^+$ calcd for $C_{25}H_{39}N_3O_5S$ 494.26; found: 494.6.

Example 4

3-endo-(8-2-[(4,4-Difluorocyclohexylmethyl)-(2-hydroxyacetyl)-amino]ethyl-8-azabicyclo[3.2.1]oct-3-yl)-2-hydroxybenzamide To a solution of 3-endo-(8-2-[(4,4-difluorocyclohexylmethyl)amino]ethyl-8-azabicyclo[3.2.1]oct-3-yl)-2-hydroxybenzamide TFA salt (15 mg, 0.028 mmol) (Preparation 9) and DIPEA (12 μL, 0.071 mmol) in DCM (5 mL) was added acetoxyacetyl chloride (4.6 μL, 0.0439 mmol). The reaction mixture was stirred for 1 h and concentrated. Methanol (2 mL) was added followed by 6 N NaOH (60 μL). The reaction mixture was stirred at room temperature for 1 h, concentrated, and purified by preparative HPLC to give the title compound as its TFA salt (9.2 mg). (m/z): [M+H]$^+$ calcd for $C_{25}H_{35}F_2N_3O_4$ 480.26; found: 480.2.

Example 5

3-endo-(8-2-[(2,2-Dimethylpropyl)-(2-hydroxyacetyl)amino]-ethyl-8-azabicyclo[3.2.1]oct-3-yl)-2-hydroxybenzamide Following the procedure of Example 4 using 3-endo-(8-[2-(2,2-dimethylpropylamino)ethyl]-8-azabicyclo[3.2.1]oct-3-yl)-2-hydroxybenzamide TFA salt (Preparation 10) in place of 3-endo-(8-2-[(4,4-difluoro -cyclohexylmethyl)amino]ethyl-8-azabicyclo[3.2.1]oct-3-yl)-2-hydroxybenzamide TFA salt, the title compound was prepared as its TFA salt. (m/z): [M+H]$^+$ calcd for $C_{23}H_{35}N_3O_4$ 418.26; found: 418.8.

Example 6

3-endo-(8-{2-[((S)-2,3-Dihydroxypropionyl)-(2,2-dimethylpropyl)amino]ethyl}-8-azabicyclo[3.2.1]oct-3-yl)-2-hydroxybenzamide Following the procedure of Example 1 using 3-endo-(8-[2-(2,2-dimethyl-propylamino)ethyl]-8-aza-bicyclo[3.2.1]oct-3-yl)-2-hydroxy-benzamide TFA (Preparation 10) in place of 3-endo-(8-[2-(2-ethylbutylamino)ethyl]-8-azabicyclo[3.2.1]oct-3-yl-2-hydroxybenzamide TFA, the title compound was prepared as its TFA salt. (m/z): [M+H]$^+$ calcd for $C_{24}H_{37}N_3O_5$ 448.27; found: 448.2.

Example 7

3-endo-(8-{2-[Cyclohexylmethyl-(2-hydroxyacetyl)amino]-ethyl}-8-azabicyclo[3.2.1]oct-3-yl)-2-hydroxybenzamide a. Acetic acid [cyclohexylmethyl-(2-hydroxyethyl)carbamoyl]-methyl ester

To a solution of 2-(cyclohexylmethylamino)-ethanol (600 mg, 3.8 mmol) in DCM (6 mL) at 0° C. was added DIPEA (588 mg, 4.6 mmol) and then acetoxyacetyl chloride (467 mg, 3.44 mmol) over 5 min. The resulting mixture was warmed to room temperature, stirred overnight under an atmosphere of nitrogen, diluted with DCM and washed successively with 1 N aqueous HCl, saturated NaHCO$_3$, and brine. The organic layer was dried over magnesium sulfate, filtered, and concentrated to yield the title compound (914 mg). (m/z): [M+H]$^+$ calcd for C$_{13}$H$_{23}$NO$_4$, 258.16; found, 258.0.

b. Acetic acid [cyclohexylmethyl-(2-oxo-ethyl)-carbamoyl]-methyl ester

To a solution of the product of the previous step (916 g, 3.56 mmol) in DCM (10 mL) at 0° C. was added sequentially DMSO (417 mg, 5.34 mmol), DIPEA(1.12 g, 8.9 mmol) and sulfur trioxide pyridium complex (1.42 g, 8.9 mmol). The reaction mixture was stirred for 72 h, diluted with DCM and washed successively with 1 N aqueous HCl and brine. The organic layer was dried over magnesium sulfate, filtered, and concentrated. The crude material was purified by flash chromatography (20 to 100% EtOAc in hexanes) to afford the title intermediate. After concentration, the title compound was obtained as dark orange oil (260 mg) and used in the next step without further purification.

c. Acetic acid ({2-[3-endo-(3-carbamoyl-2-hydroxyphenyl)-8-aza-bicyclo[3.2.1]oct-8-yl]ethyl}cyclohexylmethyl-carbamoyl)-methyl ester To a suspension of 3-endo-(8-azabicyclo[3.2.1]oct-3-yl)-2-hydroxybenzamide TFA salt (32 mg, 0.09 mmol) in DCM (0.3 mL) was added acetic acid [cyclohexylmethyl-(2-oxo-ethyl)-carbamoyl]-methyl ester (34 mg, 0.13 mmol) and DIPEA (23 mg, 0.18 mmol). The reaction mixture was stirred for 30 min, and then sodium triacetoxy borohydride (28 mg, 0.13 mmol) was added and the mixture was stirred for 1 h. The reaction mixture was diluted with DCM (1 mL) and washed with saturated sodium bicarbonate (2 mL). The organic layer was concentrated to give the title compound which was used in next step without further purification (m/z): [M+H]$^+$ calcd for C$_{27}$H$_{39}$N$_3$O$_5$, 486.29; found, 486.4.

d. 3-endo-(8-{2-[Cyclohexylmethyl-(2-hydroxy-acetyl)amino]-ethyl}-8-azabicyclo[3.2.1]oct-3-yl)-2-hydroxybenzamide The oily residue from the previous step was dissolved in ethanol (0.3 mL) and treated with LiOH.H$_2$O (10 mg, 0.5 mmol) in water (0.08 mL) for 2 h. The solvent was concentrated and the residue was dissolved in 50% acetic acid in water (1.2 mL), filtered, and purified by preparative HPLC to give the title compound as its TFA salt (22.7 mg). (m/z): [M+H]$^+$ calcd for C$_{25}$H$_{37}$N$_3$O$_4$, 444.28; found, 445.0.

Example 8

3-endo-(8-2-[(4,4-Difluoro-cyclohexylmethyl)-((S)-2,3-dihydroxy-1-oxo-propyl)-amino]-ethyl-8-aza-bicyclo[3.2.1]oct-3-yl)-2-hydroxy-benzamide To a solution of 3-endo-(8-2-[(4,4-difluoro-cyclohexylmethyl) -amino]-ethyl-8-aza-bicyclo[3.2.1]oct-3-yl)-2-hydroxy-benzamide (60.0 mg, 0.14 mmol) and Lithium (S)-2,2-dimethyl-1,3-dioxolane-4-carboxylate (32 mg, 0.21 mmol) in DMF (2 mL) was added N,N,N',N'-tetramethyl-O-(7-azabenzotriazol-1-yl)uronium hexafluorophosphate (65 mg, 0.17 mmol). The reaction mixture was stirred overnight and concentrated. The resulting solid was stirred in 1:1 AcOH:water at 70° C. overnight and purified by preparative HPLC to give the title compound as its TFA salt (65 mg) (m/z): [M+H]$^+$ calcd for C$_{26}$H$_{37}$F$_2$N$_3$O$_5$ 510.27; found 510.6.

Example 9

3-endo-(8-2-[(4,4-Difluoro-cyclohexylmethyl)-(2-methanesulfonyl-acetyl)-amino]-ethyl-8-aza-bicyclo[3.2.1]oct-3-yl)-2-hydroxy-benzamide To a solution of 3-endo-(8-2-[(4,4-difluoro-cyclohexylmethyl) -amino]-ethyl-8-aza-bicyclo[3.2.1]oct-3-yl)-2-hydroxy-benzamide (310 mg, 0.74 mmol) in DMF (2.1 mL) was added DIPEA (154 µL, 0.88 mmol) followed by methanesulfonyl-acetic acid (112 mg, 0.81 mmol) and then N,N,N',N'-tetramethyl-O-(7-azabenzotriazol-1-yl)uronium hexafluorophosphate (336 mg, 0.88 mmol). The reaction mixture was stirred overnight, concentrated, and purified by preparative HPLC to give the title compound as it TFA salt (199 mg). $^1$H NMR (CD$_3$OD, 400 mHz) δ (ppm) 7.69 (dd, J=8.0 Hz, 1.5 Hz, 1H), 7.70-7.64 (m, 2H), 7.44-7.34 (m, 3H), 7.32 (dd, J=7.5 Hz, 1.8 Hz, 1H), 6.84 (t, J=7.8 Hz, 1H), 6.6-6.1 (m, 1H), 4.12 (dd, J=17.8 Hz, 8.4 Hz, 2H), 3.80-3.68 (m, 2H), 3.18-3.06 (m, 1H), 2.46-2.30 (m, 2H), 2.29-2.14 (m, 2H), 2.03-1.93 (m, 1H). (m/z): [M+H]$^+$ calcd for C$_{26}$H$_{37}$F$_2$N$_3$O$_5$S 542.24; found 542.6.

Examples 10 and 11

Following the process of Example 9 using the appropriate 8-aza-bicyclo[3.2.1]oct-3-yl)-2-hydroxy-benzamide derivative, the TFA salts of the following compounds were prepared:

Example 10: 3-endo-(8-2-[(2,2-dimethyl-propyl)-(2-methanesulfonyl-acetyl)-amino]-ethyl-8-aza-bicyclo[3.2.1]oct-3-yl)-2-hydroxy-benzamide (m/z): [M+H]$^+$ calcd for C$_{24}$H$_{37}$N$_3$O$_5$S 480.25; found 480.0.

Example 11: 3-endo-(8-2-[cyclohexylmethyl-(2-methanesulfonyl -acetyl)-amino]-ethyl-8-aza-bicyclo[3.2.1]oct-3-yl)-2-hydroxy-benzamide (m/z): [M+H]$^+$ calcd for C$_{26}$H$_{39}$N$_3$O$_5$S 506.26; found 506.2

Example 12

3-endo-(8-2-[Cyclohexylmethyl-((S)-2,3-dihydroxy-1-oxo -propyl)-amino]-ethyl-8-aza-bicyclo[3.2.1]oct-3-yl)-2-hydroxy-benzamide Following the process of Example 8 using the appropriate 8-aza-bicyclo[3.2.1]oct-3-yl)-2-hydroxy-benzamide derivative, the TFA salt of the title compound was prepared. (m/z): [M+H]$^+$ calcd for C$_{26}$H$_{39}$N$_3$O$_5$ 474.29; found 474.2.

Example 13

3-endo-[8-(3-Benzoylamino-propyl)-8-aza-bicyclo[3.2.1]oct-3-yl]-2-hydroxy-benzamide Benzoyl chloride (5.56 µL, 0.05 mmol) was added to a solution of 3-endo -[8-(3-amino-propyl)-8-aza-bicyclo[3.2.1]oct-3-yl]-2-hydroxy-benzamide TFA (20 mg; 0.05 mmol) and DIPEA (16.7 µL, 0.10 mmol) in acetonitrile (0.50 mL) and DCM (0.50 mL). The reaction mixture was stirred for 30 min, concentrated, and purified by preparative HPLC to give the title compound as its TFA salt (16 mg). (m/z): [M+H]+ calcd for $C_{24}H_{29}N_3O_3$ 408.22; found 408.2.

Examples 14 to 18

Following the procedure of Example 13, using the appropriate acid chloride (Examples 14 to 16) or the procedure of Example 9 using 3-endo-[8-(3-amino-propyl)-8-aza-bicyclo[3.2.1]oct-3-yl]-2-hydroxy-benzamide TFA and the appropriate acid (Examples 17 and 18), the TFA salts of the compounds of Table 1 were prepared.

TABLE 1

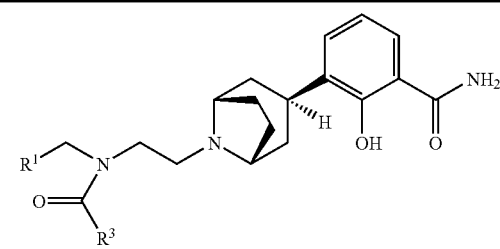

| Ex No. | R³ | Formula | Calc [M + H]+ | Found [M + H]+ |
|---|---|---|---|---|
| 14 | 3-chlorophenyl | $C_{24}H_{28}ClN_3O_3$ | 442.18 | 442.2 |
| 15 | 3,5-difluorophenyl | $C_{24}H_{27}F_2N_3O_3$ | 444.20 | 444.2 |
| 16 | 3,5-dichlorophenyl | $C_{24}H_{27}Cl_2N_3O_3$ | 476.14 | 476.2 |
| 17 | 3-fluorophenyl | $C_{24}H_{29}N_3O_3$ | 426.21 | 426.2 |
| 18 | 3-chloro-2-fluorophenyl | $C_{24}H_{27}ClFN_3O_3$ | 460.17 | 460.2 |

Example 19

N-{2-[3-endo-(3-Carbamoyl-2-hydroxy-phenyl)-8-aza-bicyclo[3.2.1]oct-8-yl]-ethyl}-N-(2-ethyl-butyl)-succinamic acid To succinic anhydride (32 mg, 0.32 mmol) was added N,N,N',N'-tetramethyl-O-(7-azabenzotriazol-1-yl)uronium hexafluorophosphate (120 mg, 0.32 mmol) followed by a solution of 3-endo-8-[2-(2-ethyl-butylamino)-ethyl]-8-aza-bicyclo[3.2.1]oct-3-yl-2-hydroxy-benzamide (58.9 mg, 0.16 mmol) and DIPEA (81 mg, 0.63 mmol) in DMF (0.5 mL). The resulting mixture was stirred at room temperature for 1 h. The reaction mixture was concentrated, dissolved in 1:1 AcOH:$H_2O$ (1.5 mL), filtered and purified by preparative HPLC to provide the title compound as its TFA salt (43.8 mg). (m/z): [M+H]+ calcd for $C_{26}H_{39}N_3O_5$ 474.29; found 474.2.

Examples 20 to 26

Following the general procedure of Example 19, the TFA salts of the compounds of Table 2 were prepared:

TABLE 2

| Ex No. | R¹ | R³ | Formula | Calc [M + H]+ | Found [M + H]+ |
|---|---|---|---|---|---|
| 20 | 1-ethylpropyl | —CH₂C(O)OH | $C_{25}H_{37}N_3O_5$ | 460.27 | 460.2 |
| 21 | 1-ethylpropyl | —CH₂C(O)O-benzyl | $C_{32}H_{43}N_3O_5$ | 550.32 | 550.2 |
| 22 | 4,4-diF-chexyl | —CH₂C(O)O-benzyl | $C_{33}H_{41}F_2N_3O_5$ | 598.30 | 598.2 |
| 23 | 4,4-diF-chexyl | —CH₂C(O)OH | $C_{26}H_{35}F_2N_3O_5$ | 508.25 | 508.2 |
| 24 | 4,4-diF-chexyl | —(CH₂)₂C(O)OH | $C_{27}H_{37}F_2N_3O_5$ | 522.27 | 522.2 |
| 25 | t-butyl | —CH₂C(O)O-benzyl | $C_{31}H_{41}N_3O_5$ | 536.30 | 536.2 |
| 26 | t-butyl | —CH₂C(O)OH | $C_{24}H_{35}N_3O_5$ | 446.26 | 446.2 |

Assay 1: Radioligand Binding Assay on Human Mu, Human Delta and Guinea Pig Kappa Opioid Receptors a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin–100 µg/mL streptomycin and 800 µg/mL Geneticin in a 5% $CO_2$, humidified incubator @ 37° C. Receptor expression levels ($B_{max}$~2.0 and ~0.414 pmol/mg protein, respectively) were determined using [³H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 µL containing the appropriate amount of membrane protein (~3, ~2 and ~20 µg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 µM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM naloxone. $K_i$ values for test compounds were calculated, in Prism, from the best fit $IC_{50}$ values, and the $K_d$ value of the radioligand, using the Cheng-Prusoff equation ($K_i=IC_{50}/(1+([L]/K_d))$ where [L]=the concentration of [$^3$H]-Diprenorphine. Results are expressed as the negative decadic logarithm of the $K_i$ values, $pK_i$.

Test compounds having a higher $pK_i$ value in these assays have a higher binding affinity for the mu, delta, or kappa opioid receptor. The compounds of Examples 1-26 were tested in these assays. All of the compounds had a $pK_i$ value between about 8.4 and about 10.7 at the human mu opioid receptor. For example, the compounds of Examples 1, 2, and 6 had $pK_i$ values of 10.0, 10.0, and 9.6, respectively. Compounds of the invention also exhibited $pK_i$ values between about 7.5 and about 10.2 at the human delta and guinea pig kappa opioid receptors.

Assay 2: Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound [$^{35}$S]GTPγS present following receptor activation in membranes prepared from CHO-K1 cells expressing the human mu opioid receptor.

a. Mu Opioid Receptor Membrane Preparation:

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 pmol/mg protein, respectively. Protein concentration was determined using a Bio-Rad Bradford Protein Assay kit. Membranes were stored in frozen aliquots at −80° C., until required.

b. Human Mu [$^{35}$S]GTPγS Nucleotide Exchange Assay

Membranes were prepared as described above, and prior to the start of the assay, aliquots were diluted to a concentration of 200 µg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 µM into Assay Buffer containing 0.1% BSA, and serial (1:5) dilutions then made to generate ten concentrations of compound ranging from 40 µM-80 µM. GDP and [$^{35}$S]GTPγS were diluted to 40 µM and 0.4 nM, respectively, in Assay Buffer. The assay was performed in a total volume of 200 µL containing 10 µg of membrane protein, test compound ranging from 10 µM-20 µM), 10 µM GDP, and 0.1 nM [$^{35}$S]GTPγS diluted in 10 mM $MgCl_2$, 25 mM NaCl, and 0.0125% BSA (final assay concentrations). A DAMGO (Tyr-D-Ala-Gly-(methyl)Phe -Gly-ol) concentration-response curve (ranging from 12.8 pM-1 µM) was included on every plate.

Assay plates were prepared immediately prior to assay following the addition of 50 µL of the $NaCl/MgCl_2/GDP$ solution, 50 µL of test compound, and 50 µL of [$^{35}$S]GTPγS. The assay was initiated by the addition of 50 µL of membrane protein and allowed to incubate for 30 minutes at room temperature. The reaction was terminated by filtration onto 96-well GF/B filter plates, pre-blocked with 0.3% polyethylenimine, using a Packard Filtermate harvester, and wash with ice-cold Assay Buffer (3×200 µl). Plates are dried overnight prior to determination of counts bound via liquid scintillation on a Packard Topcount instrument. Vehicle: DMSO not to exceed 1% final assay concentration.

The amount of bound [$^{35}$S]GTPγS is proportional to the degree of activation of the mu opioid receptors by the test compound. The intrinsic activity (IA), expressed as a percentage, was determined as the ratio of the amount of bound [$^{35}$S]GTPγS observed for activation by the test compound to the amount observed for activation by DAMGO which is presumed to be a full agonist (IA=100). The compounds of the invention tested in this assay demonstrated intrinsic activities of less than about 10. For example, the compounds of Examples 1, 3, and 6 had IA values of −1, −4, and 9, respectively. Thus, the compounds of the present invention have been shown to act as antagonists at the human mu opioid receptor.

Assay 3: Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (®1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit $ID_{50}$ values were calculated. Curve minima and maxima were fixed to loperamide control values (indicating 0% reversal) and vehicle controls (indicating 100% reversal), respectively. Results are expressed as $ID_{50}$, the dose required for 50% reversal of the effects of loperamide, in milligrams per kilogram. The compounds of Examples 1, 4, and 6 administered orally, exhibited $ID_{50}$ values of 0.11 mg/kg, 0.014 mg/kg. and 0.42 mg/kg, respectively in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

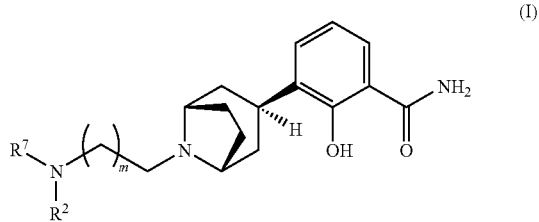

(I)

wherein:
$R^7$ is hydrogen or —CH$_2$—R$^1$;
$R^1$ is $C_{4-10}$ alkyl, $C_{3-12}$cycloalkyl, or phenyl, wherein $C_{3-12}$cycloalkyl and phenyl are each optionally substituted with one or two halo;
$R^2$ is selected from —C(O)R$^3$, —C(O)NHR$^4$, —C(O)OR$^5$, —S(O)$_2$R$^6$, and —C(O)R$^8$;
$R^3$ is $C_{1-6}$ alkyl substituted with one or two substituents selected from —OR$^a$, —S(O)$_2$R$^b$, and —C(O)R$^c$;
$R^4$ and $R^5$ are each independently $C_{1-6}$ alkyl substituted with one or two substituents selected from —OR$^a$ and —S(O)$_2$R$^b$;
$R^6$ is $C_{1-3}$alkyl;
$R^8$ is phenyl, optionally substituted with one or two halo;
$R^a$ is hydrogen or $C_{1-3}$alkyl;
$R^b$ is $C_{1-3}$alkyl;
$R^c$ is selected from hydrogen, $C_{1-3}$alkyl, and benzyl; and
m is 1 or 2;
provided that when $R^7$ is hydrogen, $R^2$ is —C(O)R$^8$;
or a pharmaceutically-acceptable salt thereof.

2. The compound of claim 1 wherein the compound of formula (I) is a compound of formula (Ia):

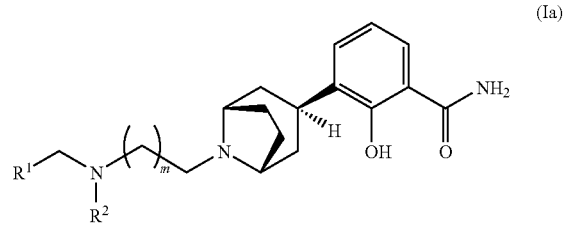

(Ia)

wherein:
$R^2$ is selected from —C(O)R$^3$, —C(O)NHR$^4$, —C(O)OR$^5$, and —S(O)$_2$R$^6$; and
$R^3$, $R^4$, and $R^5$ are each independently $C_{1-6}$ alkyl substituted with one or two substituents selected from —OR$^a$ and —S(O)$_2$R$^b$;
or a pharmaceutically-acceptable salt thereof.

3. The compound of claim 2 wherein $R^1$ is $C_{4-6}$alkyl or $C_{3-6}$cycloalkyl, wherein $C_{3-6}$cycloalkyl is optionally substituted with one or two fluoro.

4. The compound of claim 2 wherein $R^1$ is 1-ethylpropyl, tert-butyl, cyclohexyl, or 4,4-difluorocyclohexyl.

5. The compound of claim 2 wherein the compound of formula (Ia) is a compound of formula (Ic):

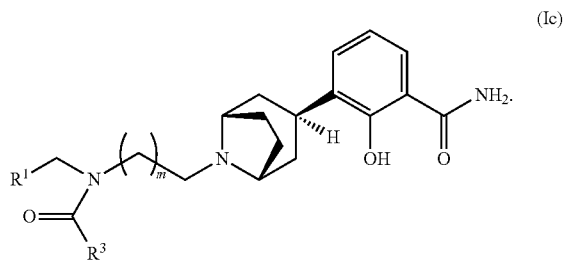

(Ic)

6. The compound of claim 5 wherein $R^3$ is $C_{1-3}$alkyl substituted with one or two —OH or with one —S(O)$_2$CH$_3$.

7. The compound of claim 1 wherein the compound is selected from:
3-endo-(8-{2-[((S)-2,3-dihydroxypropionyl)-(2-ethylbutyl)-amino]ethyl}-8-azabicyclo[3.2.1]oct-3-yl)-2-hydroxybenzamide;
3-endo-(8-2-[(2-ethylbutyl)-(2-hydroxyacetyl)amino]-ethyl-8-azabicyclo[3.2.1]oct-3-yl)-2-hydroxybenzamide;
3-endo-(8-2-[(2-ethylbutyl)-(2-methanesulfonylacetyl)amino]ethyl-8-aza-bicyclo[3.2.1]oct-3-yl)-2-hydroxybenzamide;
3-endo-(8-2-[(4,4-difluorocyclohexylmethyl)-(2-hydroxyacetyl)-amino]ethyl-8-azabicyclo[3.2.1]oct-3-yl)-2-hydroxybenzamide;
3-endo-(8-2-[(2,2-dimethylpropyl)-(2-hydroxyacetyl)amino]-ethyl-8-azabicyclo[3.2.1]oct-3-yl)-2-hydroxybenzamide;
3-endo-(8-{2-[((S)-2,3-dihydroxypropionyl)-(2,2-dimethylpropyl)amino]ethyl}-8-azabicyclo[3.2.1]oct-3-yl)-2-hydroxybenzamide;
3-endo-(8-{2-[cyclohexylmethyl-(2-hydroxyacetyl)amino]-ethyl}-8-azabicyclo[3.2.1]oct-3-yl)-2-hydroxybenzamide;

3-endo-(8-2-[(4,4-difluorocyclohexylmethyl)-((S)-2,3-dihydroxy-1-oxo-propyl)-amino]-ethyl-8-aza-bicyclo[3.2.1]oct-3-yl)-2-hydroxybenzamide; and 3-endo-(8-2-[(4,4-difluorocyclohexylmethyl)-(2-methanesulfonylacetyl)-amino]-ethyl-8-aza-bicyclo[3.2.1]oct-3-yl)-2-hydroxybenzamide;

and pharmaceutically-acceptable salts thereof.

8. A pharmaceutical composition comprising the compound of claim 1 and a pharmaceutically acceptable carrier.

9. A pharmaceutical composition comprising the compound of claim 7 and a pharmaceutically acceptable carrier.

10. A process for preparing a compound of formula (Id),

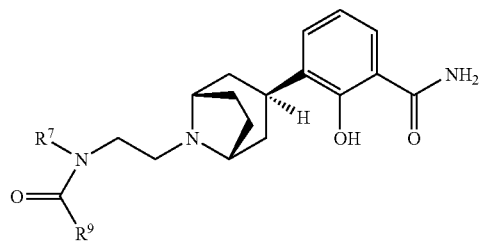

or a pharmaceutically-acceptable salt or protected derivative thereof, wherein $R^7$ is hydrogen or —$CH_2$—$R^1$;

$R^1$ is $C_{4-10}$ alkyl, $C_{3-12}$cycloalkyl, or phenyl, wherein $C_{3-12}$cycloalkyl and phenyl are each optionally substituted with one or two halo;

$R^9$ is $R^3$ or $R^8$;

$R^3$ is $C_{1-6}$ alkyl substituted with one or two substituents selected from —$OR^a$, —$S(O)_2R^b$, and —$C(O)R^c$;

$R^8$ is phenyl, optionally substituted with one or two halo;

$R^a$ is hydrogen or $C_{1-3}$alkyl;

$R^b$ is $C_{1-3}$alkyl;

$R^c$ is selected from hydrogen, $C_{1-3}$alkyl, and benzyl; and m is 1 or 2;

provided that when $R^7$ is hydrogen, $R^2$ is —$C(O)R^8$;

the process comprising:
(a) reacting a compound of formula (II):

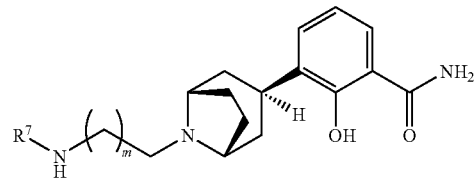

with a compound of formula $R^{9a}C(O)$-L wherein $R^{9a}$ is $R^3$, a protected form of $R^3$, or $R^8$, and L represents a leaving group or $R^{9a}C(O)$-L represents a carboxylic acid; and (b) optionally deprotecting the product of the reaction, to provide a compound of formula (I) or a pharmaceutically-acceptable salt or protected derivative thereof.

11. The process of claim 10 wherein $R^7$ is —$CH_2$—$R^1$, $R^9$ is $R^3$, and $R^{9a}$ is $R^3$ or a protected form of $R^3$.

12. A compound of formula (II):

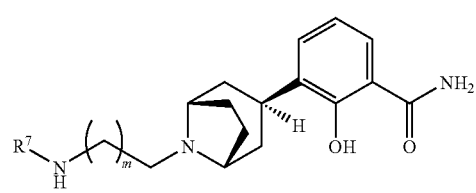

wherein
$R^7$ is hydrogen or —$CH_2$—$R^1$;
$R^1$ is $C_{4-10}$ alkyl, $C_{3-12}$cycloalkyl, or phenyl, wherein $C_{3-12}$cycloalkyl and phenyl are each optionally substituted with one or two halo; and
m is 1 or 2.

13. The compound of claim 12 wherein $R^7$ is —$CH_2$—$R^1$.

14. A compound of formula (IV):

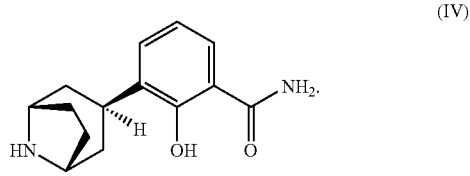

* * * * *

UNITED STATES PATENT AND TRADEMARK OFFICE
CERTIFICATE OF CORRECTION

| | | |
|---|---|---|
| PATENT NO. | : 7,902,220 B2 | Page 1 of 1 |
| APPLICATION NO. | : 12/229664 | |
| DATED | : March 8, 2011 | |
| INVENTOR(S) | : Daisuke Roland Saito et al. | |

It is certified that error appears in the above-identified patent and that said Letters Patent is hereby corrected as shown below:

At Column 41, line 51, "$R^2$ is -C(O)$R^8$" should be "$R^9$ is $R^8$".

Signed and Sealed this
Thirteenth Day of March, 2012

David J. Kappos
*Director of the United States Patent and Trademark Office*